US009815921B2

(12) United States Patent
Yim et al.

(10) Patent No.: US 9,815,921 B2
(45) Date of Patent: Nov. 14, 2017

(54) CONSTRUCT FOR PROMOTING ABSORPTION OF MOLECULES BY A CELL AND METHODS OF USING THE CONSTRUCT

(75) Inventors: King Fai Evelyn Yim, Singapore (SG); Hong Yee Low, Singapore (SG); Tanu Suryadi Kustandi, Singapore (SG); Kim Kiat Teo, Singapore (SG); Seok Hong Goh, Singapore (SG)

(73) Assignees: **AGENCY FOR SCIENCE, TECHNOLOGY AND RESEARCH (A*STAR), Singapore (SG); NATIONAL UNIVERSITY OF SINGAPORE**, Singapore (SG)

( * ) Notice: Subject to any disclaimer, the term of this patent is extended or adjusted under 35 U.S.C. 154(b) by 37 days.

(21) Appl. No.: 13/602,616

(22) Filed: Sep. 4, 2012

(65) Prior Publication Data
US 2013/0244889 A1    Sep. 19, 2013

Related U.S. Application Data

(60) Provisional application No. 61/529,969, filed on Sep. 1, 2011.

(51) Int. Cl.
| | | |
|---|---|---|
| *A61M 5/32* | (2006.01) | |
| *B29D 7/00* | (2006.01) | |
| *C08F 112/08* | (2006.01) | |
| *G03F 7/00* | (2006.01) | |
| *C12N 5/00* | (2006.01) | |

(52) U.S. Cl.
CPC .......... *C08F 112/08* (2013.01); *C12N 5/0068* (2013.01); *G03F 7/0002* (2013.01); *C12N 2533/30* (2013.01); *C12N 2535/00* (2013.01); *Y10T 428/24355* (2015.01)

(58) Field of Classification Search
CPC ... C08F 112/08; C12N 2535/10; G03F 7/0002
USPC .......................................................... 506/7
See application file for complete search history.

(56) References Cited

U.S. PATENT DOCUMENTS

| | | | | |
|---|---|---|---|---|
| 2004/0125266 | A1* | 7/2004 | Miyauchi .......... | B01L 3/502761 349/57 |
| 2005/0214935 | A1* | 9/2005 | Kuwabara et al. ........ | 435/299.1 |
| 2008/0269685 | A1* | 10/2008 | Singh ................... | A61K 9/0021 604/173 |
| 2009/0043279 | A1* | 2/2009 | Kaspar ................. | A61K 9/0021 604/506 |

(Continued)

FOREIGN PATENT DOCUMENTS

WO    2008115160 A1    9/2008

OTHER PUBLICATIONS

Shalek et al. (PNAS, 2010, vol. 107, No. 5, pp. 1870-1875, "Vertical silicon nanowires as a universal platform for delivering biomolecules into living cells").*

(Continued)

*Primary Examiner* — Karla Dines
(74) *Attorney, Agent, or Firm* — Conley Rose, P.C.

(57) ABSTRACT

The present invention is directed to a construct for promoting absorption of molecules by a cell and the application thereof in drug and gene delivery. The present invention further describes topographical modulation of endocytosis for drug and gene delivery.

20 Claims, 22 Drawing Sheets

(56) References Cited

U.S. PATENT DOCUMENTS

2010/0061962 A1* 3/2010 Li .......................... A61L 27/18
424/93.7

OTHER PUBLICATIONS

Hochbaum et al. (Nano Letters, 2005, vol. 5, No. 3, pp. 457-460, "Controlled growth of Si nanowire arrays for device integration").*
Hulteen et al. (Journal of Vacuum Science and Technology A, 1995, vol. 13, No. 3, pp. 1553-1558, "Nanosphere lithography; a materials general fabrication process for periodic particle array surfaces").*
McKnight et al. (Nano letters, 2004, vol. 4, No. 7, pp. 1213-1219, "Tracking gene expression after DNA delivery using spatially indexed nanofiber arrays").*
Porter et al. (Biomaterials, 2009, vol. 30, pp. 780-788, "Biodegradable poly(ε-caprolactone) nanowires for bone tissue engineering").*
Zhu et al. (Nanoscale, 2011, vol. 3, pp. 2723-2729, "Creation of nanostructures by interference lithography for modulation of cell behavior").*
Choi et al. (Nano Letters, 2008, vol. 8, No. 11, pp. 37899-3802, "Synthesis of silicone nanowires and nanofin arrays using Interference Lithography and Catalytic Etching").*
Goryu et al. (IEEETransducers20111741-1744, "Electrical catching and transfer of nanoparticles via nanotip silicone probe arrays").*
Berthing et al., (Journal of Nanoneuroscience, 2009, vol. 1, pp. 3-9, "Applications of nanowire arrays in nanomedicine").*
Borkowf et al., (Calcified Tissue International, 1987, vol. 40, pp. 173-176, "Endocytosis is required for the mitogenic effect of basic calcium phosphate crystals in fibroblasts").*
Gerasimenko et al., (Current Biology, 1998, vol. 8, pp. 1335-1338, "calcium uptake via endocytosis with rapid release from acidifying endosomes").*
Blumhoff et al. (Science, 1990, vol. 250, pp. 399-404, "transport and storage of vitamin A").*
Dalby et al. I (Biomaterials, 2003, vol. 23, pp. 927-935, "Fibroblast reaction to island topography: changes in cytoskeleton and morphology with time").*
Lan et al., Lithography, edited by Michael Wang, Feb. 2010, Chapter 23, pp. 457-494.*
Chandra et al. (Soft Matter, 2008, 4, pp. 979-984).*
Yim, Evelyn, et al., Significance of synthetic nanostructures in dictating cellular response, Nanomedicine: Nanotechnology, Biology, and Medicine 1 (2005) pp. 10-21 (12 pages).
Kim, Sun Min, et al., Patterned Cocultures for Controlling Cell-Cell Interactions, Chapter 4 Patterned Cocultures for Controlling Cell-Cell Interactions, pp. 53-70 (18 pages).
Search Report and Written Opinion dated Oct. 3, 2013 (14 pages).
Kim, Evelyn K.F. et al., Nanotopography-induced changes in focal adhesions, cytoskeletal organization, and mechanical properties of human mesenchymal stem cells, Biomaterials 31 (2010) pp. 1299-1306 (8 pages).
Dalby, Matthew J., et al., Attempted endocytosis of nano-environment produced by colloidal lithography by human fibroblasts, Exp. Cell Res. 295 (2004) pp. 387-394 (8 pages).
Saez, Alexandre, et al., Rigidity-driven growth and migration of epithelial cells on microstructured anisotropic substrates, Proc. Natl. Acad. Sci. U.S.A. 20 (2007) pp. 8281-8286 (6 pages).
Adler, Andrew F., et al., High-throughput screening of microscale pitted substrate topographies for enhanced nonviral transfection efficiency in primary human fibroblasts, Biomaterials 32 (2011) pp. 3611-3619 (9 pages).
Yim, E. K. et al., Significance of synthetic nanostructures in dictating cellular response. Nanomedicine: 1 (2005) 10-21, pp. 12-13, Abstract (1 page) may be obtained from at URL: http://www.ncbi.nlm.nih.gov/pubmed/17292053.

* cited by examiner

200nm Residual-Free Upright Pillars hMSC

2μm Collapsed Pillars

COS7

2μm Collapsed Pillars
MCF7

2μm Collapsed Pillars hMSC

(C)

2μm collapsed Pillars

CONSTRUCT FOR PROMOTING ABSORPTION OF MOLECULES BY A CELL AND METHODS OF USING THE CONSTRUCT

CROSS-REFERENCE TO RELATED APPLICATIONS

This application claims the benefit of priority of U.S. provisional application No. 61/529,969 filed on 1 Sep. 2011, the contents of it being hereby incorporated by reference in its entirety for all purposes.

FIELD OF THE INVENTION

The present invention relates to the field of devices for supporting growth and modification of biological cells.

BACKGROUND OF THE INVENTION

The topography of extracellular microenvironment can influence cellular responses from attachment and migration to differentiation and production of new tissue. Cells in their natural environment interact with extracellular matrix that contains structures in the nanometer scale. Likewise, cells cultured on surfaces with nanotopography show alteration in their biological properties with respect to attachment, motility and proliferation and the like.

In particular, endocytocytic properties of cells are also modulated in response to the topography of the extracellular environment. Recent studies have highlighted the influence of cell-topography interactions on the modulation of cellular processes, including protein expression and cytoskeletal behaviors implicated in endocytosis. Endocytosis plays a key role in intracellular molecular, drug and gene (or nucleic acid) delivery. However, topographical control of cell transfectability remains largely unexplored.

Delivery of molecules, drugs and genes to a cell can be classified into viral and non-viral vector delivery. Viral delivery provides good transfection efficiency. However, the risk of potential adverse immunological responses has hindered its development in clinical settings.

Non-viral delivery has been shown to be safe as it avoids the complication of using viral components. However, very low transfection efficiency and non-specific delivery have limited the practical application of non-viral delivery methods.

There is therefore a need to provide an improved delivery technique that overcomes the disadvantages mentioned above to enhance intracellular delivery of molecules, drugs and nucleic acids.

SUMMARY OF THE INVENTION

According to a first aspect, there is provided a construct for promoting absorption of molecules by a cell located at the surface of the construct; wherein the construct comprises:
  a plurality of micro and/or nanoscale protrusions located at the surface of the construct;
  wherein the protrusions have a size and are spaced apart from each other at a distance that promotes absorption of molecules by said cell.

According to a second aspect, there is provided a method of promoting absorption of molecules by cells, wherein the method comprises:
  providing a construct as defined above;
  seeding and culturing at least one cell at the surface of the construct under conditions suitable for absorption of molecules by the cells.

According to a third aspect, there is provided a method of cell transfection, or drug-delivery or high-throughput screening arrays using a construct as defined above.

BRIEF DESCRIPTION OF THE DRAWINGS

The invention will be better understood with reference to the detailed description when considered in conjunction with the non-limiting examples and the accompanying drawings, in which:

FIG. 3 comprises FIGS. 3A and 3B. FIG. 3 presents the flow cytometry analysis of FITC-dextran internalization in COS 7 fibroblastic cells cultured on various topographies using two different FITC-dextran tracers of different molecular weights after 24 hours of incubation time. Low MW refers to 40,000 while high MW refers to 500,000 in molecular weight.

DEFINITIONS

Figure 1:
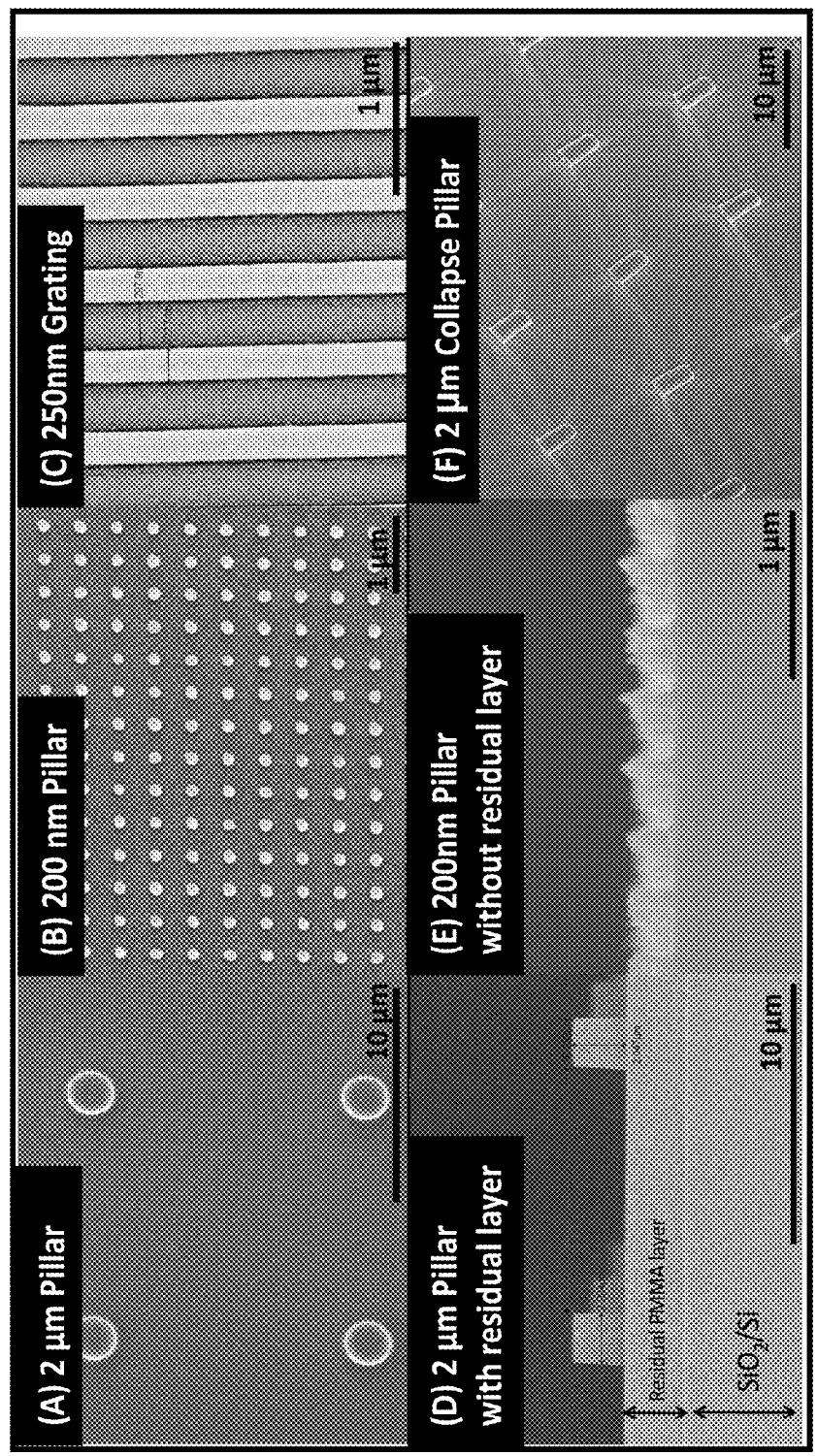
FIG. 1 shows the verification of topographical structures on the substrate. Scanning electron microscopy of poly (methyl methacrylate) (PMMA) nano- and micro-structures used in this study shows (A) a 2 μm diameter pillar with 2 μm height (top view), (B) a 200 nm diameter pillar with 400 NM height (top view), (C) a 250 nm grating with 250 nm height (top view), (D) 2 μm PMMA pillars with residual layer (cross sectional view), (E) 200 nm Rhodamine-PS pillar without residual layer (cross sectional view) and (F) 2 μm Rhodamine-polystyrene collapse pillar (top view). It can be seen from FIG. 1 that all SEM images showed high fidelity and dimensions that were in accordance to the initial mold used.

The following words and terms used herein shall have the meaning indicated:

The terms "promoting" or "promotion" indicate that uptake of molecules is possible or is improved or enhanced as determined by comparison to a control, wherein the control is an unpatterned surface.

The term "endocytosis" refers to the process where eukaryotic cells internalize segments of plasma membrane, cell-surface receptors and other essential soluble components such as nutrients from the extracellular fluid. Different regions of the plasma membrane of polarized cells, such as epithelial and endothelial cells, exhibit different biochemistry and endocytic mechanisms. Endocytosis activity at the basal-lateral surface (side interacting with the basement membrane) may be distinct from that at the apical surface. The endocytic pathway, surface receptor expression and functions may be different in the different regions of plasma membrane and in various cell types.

Endocytosis mechanisms may include but are not limited to receptor mediated endocytosis, pinocytosis and phagocytosis.

Examples of receptor mediated endocytosis may include but are not limited to caveolae-mediated endocytosis and clathrin-mediated endocytosis.

Caveolae-mediated endocytosis is defined by the involvement of flask-shape pits in the membrane known as caveolae to uptake extracellular molecules.

Clathrin-mediated endocytosis is defined by the involvement of vesicles that have a coat made up of a complex of proteins that are mainly associated with the cytosolic protein clathrin. Clathrin-mediated endocytosis is involved in Lipofectamine 2000 aided transfection.

"Pinocytosis" refers to the non-receptor mediated process where cells can uptake large volumes of extracellular fluids and materials. Pinocytosis of large volumes is also known as macropinocytosis. Macropinosomes can be >1 µm in diameter. Pinocytosis uses a mechanism which involves active formation of plasma membrane ruffles and protrusions. Macropinocytosis is one of the processes involved in FITC-dextran internalization.

Phagocytosis may refer to the process by which cells bind and internalize large particulate matter (>1 μm).

The term "microscale" is to be interpreted to include any dimensions that are in the range of about 1 μm to about 1000 μm.

The term "nanoscale" or "submicron" is to be interpreted to include any dimensions that are below 1 μm.

The term "protrusion" is to be broadly interpreted as any topographical formation on a surface extending away from the surface and/or above the surface.

The terms "isotropic" and "anisotropic" refer to uniform and non-uniform arrangements of the protrusions respectively. Uniform arrangement may include an ordered array of protrusions or other topographical structures. Non-uniform arrangement may include a disordered or random array of protrusions or other topographical structures. Uniform may also refer to the height, width, diameter, pitch or shape of the protrusions.

The term "pillar" refers to a substantially vertical structure extending from the surface of the construct.

The term "grating" refers to a series of parallel disposed grooves or slit formations on the surface of a solid surface having dimensions in the micro and/or nanoscale range.

The term "biodegradable" refers to the ability to be broken down by biological means.

The term "tissue culture grade" refers to a substrate suitable for culturing cells and tissues in vitro.

The term "basolateral cells" refer to cells that interact with the basal membrane. Examples include but are not limited to acinar cells, lacrimal acinar cells, gastrointestinal epithelial cells, skin keratinocytes and retinal pigment epithelium.

The term "apical cells" refer to cells that are located at the opposite pole of a biological structure relative to the basal membrane. Apical cells generally refer to cells that interact with a lumen of a biological structure for example, the intestine and blood vessels. Examples of apical cells include but are not limited to apical corneal epithelial cells and cells of the intestinal villi.

The present application does not only enable promoting absorption of molecules by basolateral and apical cells located or growing on the construct of the present invention but all types of cells. Thus, not only polarized cells, such as basolateral cells, can be used but also cells which are not polarized. Cells which are not polarized, upon attachment to the extracellular matrix or a substrate in vitro, the side or the area of the cell surface interacting with the substrate would be defined as "basal" membrane. Therefore, the application is not limited only to polar cells or basolateral cells. For example, fibroblasts, which are not polarized cells, have been shown in the experiments to have interaction with the nano-imprinted substrate; the cell surface that interacted with the imprinted substrate would be referred to as "basal" or "basolateral"; and the internalization through the cell-substrate interacting surface would be referred to as "basolateral internalization" or "basolateral endocytosis".

As used herein, the term "nucleic acid" means any single or double-stranded RNA or DNA molecule, such as mRNA, cDNA, genomic DNA and xeno DNA.

The term "nucleic acid vector" refers to a nucleic acid molecule that is used to introduce foreign genetic material into a target cell.

The term "siRNA" refers to small interfering ribonucleic acids (RNA) or RNA analogs comprising between about 10 to 50 or 10 to 30 nucleotides (or nucleotide analogs) capable of directing or mediating the RNA interference pathway. These molecules can vary in length and can contain varying degrees of complementarity to their target messenger RNA (mRNA). The term "siRNA" includes duplexes of two separate strands, i.e. double stranded RNA, as well as single strands that can form hairpin structures comprising of a duplex region.

The term "miRNA" refers to micro RNA. miRNA is generally a single stranded molecule that averages about 20 nucleic acids.

The term "nanoparticles" refers to particles comprising nanoscale or submicron features.

The term "microparticles" refers to particles comprising microscale features.

The term "quantum dots" refer to tiny particles of a semiconductor material, traditionally chalcogenides (selenides or sulfides) of metals like cadmium or zinc (CdSe or ZnS, for example), which range from 2 to 10 nanometers in diameter.

The term "aptamer" refers to nucleic acids or peptides having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule.

An aptamer may be a nucleic acid aptamer or a peptide aptamer. A nucleic acid aptamer refers to a nucleic acid that binds a target molecule through a mechanism which predominantly depends on Watson/Crick base pairing or triple helix binding, wherein the aptamer does not have the known physiological function of binding the target molecule. A peptide aptamer refers to combinatorial recognition molecules that consist of a constant scaffold protein, typically thioredoxin (TrxA) which contains a constrained variable peptide loop inserted at the active site.

The term "growth factor" refers to a substance that is capable of stimulating cellular growth, proliferation or cellular differentiation. Growth factors typically act as signaling molecules between cells. Examples of growth factors include but are not limited to bone morphogenic protein, fibroblast growth factor and vascular endothelial growth factor.

The term "high-throughput screening" refers to experimental methods that involve rapid collection of large amounts of data. High throughput assays employ robotics, data processing and control software, liquid handling devices, and sensitive detectors to generate and process data.

The term "attached" as used herein refers to the binding of a molecule onto a surface via chemical bonding.

The term "immobilized" as used herein refers to the adhesion of a molecule onto a surface wherein the adhesion does not involve chemical bonding.

The term "transformation" or "transformed", as used herein, refers to the genetic alteration of a cell resulting from the uptake, incorporation and expression of exogenous genetic material (for example exogenous DNA).

The term "biocompatible" as used herein refers to the property of a material that does not cause adverse biological reactions to the human or animal body.

The terms "nanoimprinting lithography" or "NIL" refers to nano-fabrication that allows the production of nano- to micron-scale features with complex structures on a wide range of materials.

The term "thermal NIL," refers to a hot embossing process wherein the pattern is frozen-in once the material is cooled down.

The term "UV-NIL" refers to imprinting that uses UV-curable resin, where the resin is polymerized/cured in-situ during the imprint process.

DETAILED DESCRIPTION OF THE PRESENT INVENTION

Exemplary, non-limiting embodiments of a construct for promoting absorption of molecules by a cell located at the surface of the construct will now be disclosed. In one embodiment, the construct comprises:
    a plurality of micro and/or nanoscale protrusions located at the surface of the construct;
    wherein the protrusions have a size and are spaced apart from each other at a distance that promotes absorption of molecules by said cell.

In one embodiment, the absorption of molecules is facilitated by endocytosis, or receptor mediated endocytosis, or pinocytosis, or phagocytosis.

In one embodiment, the protrusions are arranged in an isotropic or anisotropic pattern.

In one embodiment, the isotropic pattern may be a uniform or ordered array of protrusions.

Also, the maximum number of protrusions, such as pillars is only limited by the sample area. For example, if the sample area is 2 cm×2 cm, and the pitch of 200 nm pillar pattern is 400 nm, the total number of pillar per row will be 2 cm/400 nm, which will be 50000. Therefore, it could be 50000×50000. A typical cell culture area can be ranged from 0.5 cm$^2$ to 150 cm$^2$, Thus, it can be range up to ~500,000× ~500,000. Generally, the size and shape of the sample area of the construct thus depends on the application and the platform on which this construct is used. For example, the construct can be part of a device for high-throughput screening. Such a device can comprise multiple constructs. The multiple constructs can be either used for locating the same or different cell types on its surface.

In a further embodiment, the protrusions may have a density of 2 or more, or from 2 to 10, from 2 to 20, from 2 to 30, from 2 to 40, from 2 to 50, from 2 to 60, from 2 to 70, from 2 to 80, from 2 to 90 or from 2 to 100 protrusions in a defined area. Generally, the density will depend on the pitch size and sample area size. For example, for 1 mm×1 mm sample, using the 400 nm pitch as an example, it will be 50000. Thus, it could also range from 2 to 50000.

Figure 12:
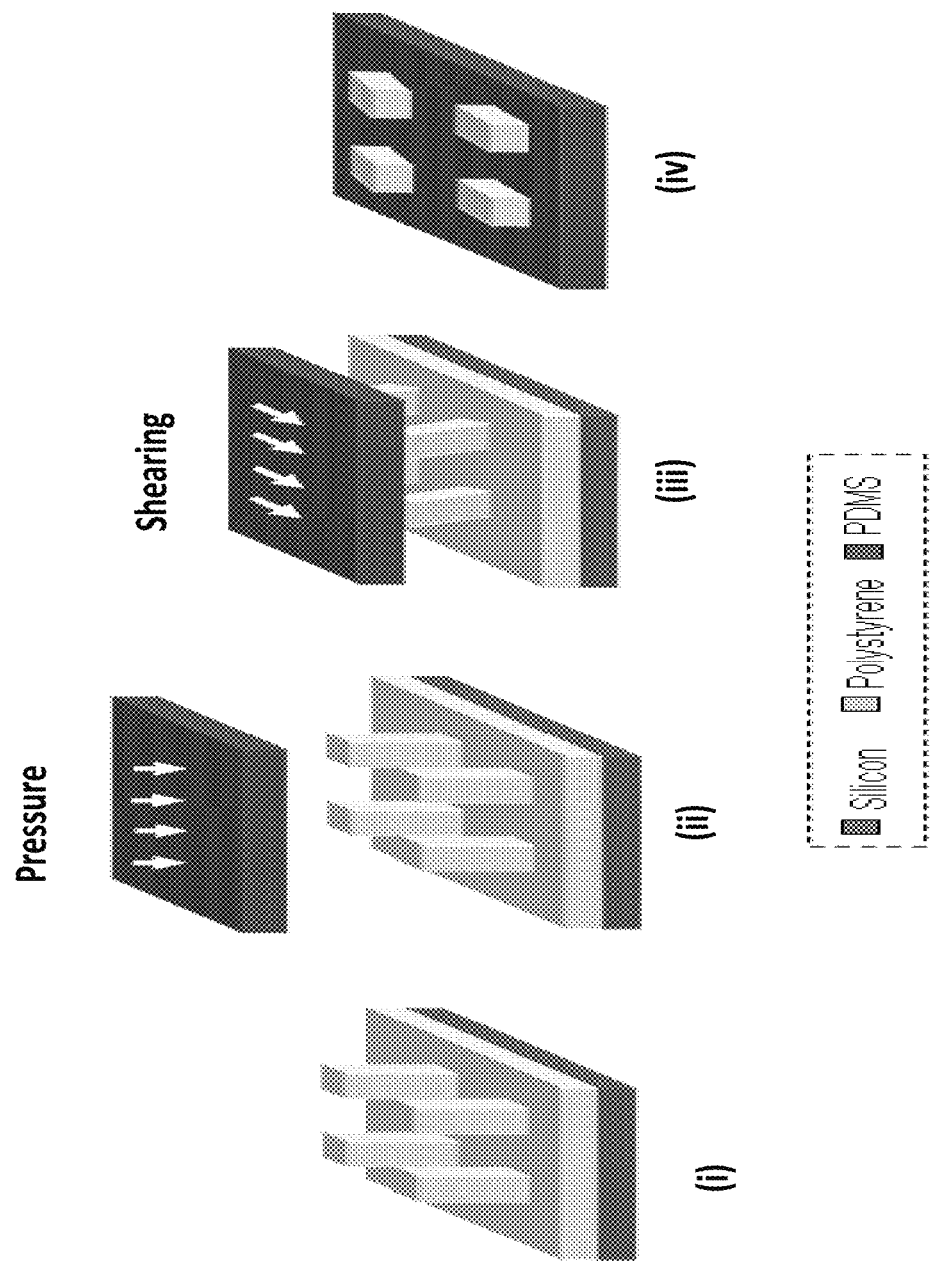
FIG. 12 shows a schematic diagram of the fabrication process for collapsed polystyrene (PS) structures. (i) Upright PS pillar structures were first fabricated using nanoimprinting lithograpy; (ii) contact initiation between the top surface of PS pillars and PDMS slab; (iii) breaking of PS upright structures via shearing; (iv) transferring collapsed PS pillars onto the PDMS slab during the process of shearing. The collected PS pillars are then used for subsequent studies.
Figure 13:
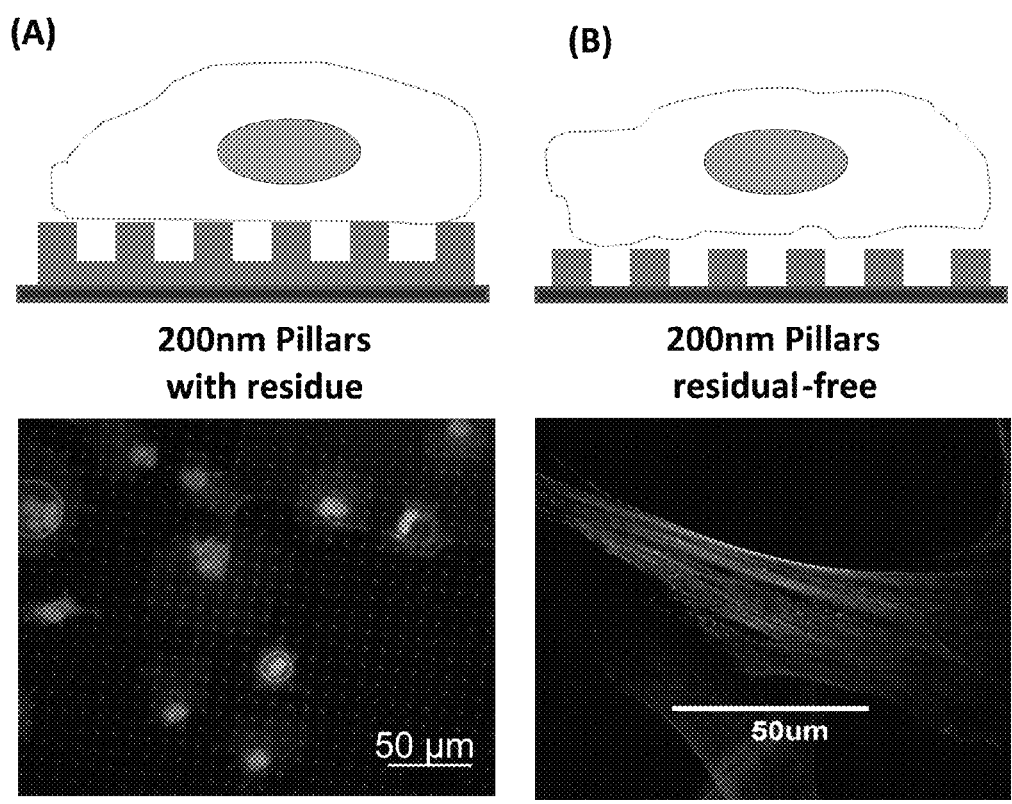
FIG. 13 shows the summary of the various substrates used for baso-lateral phagocytosis study. The top row shows the schematic diagram of the cross-section of the substrate used while the bottom row shows the representative images that were discussed relevant to the corresponding substrates. The substrates that were used were mainly those of 200 nm pillars with residue (A), 200 nm pillars residual-free (B) and 2 µm collapsed structures (C). Note the residual-free topographical structures comparing A and B while in C the topographical structures were detached from the underlying material for easy internalization.
Figure 13:
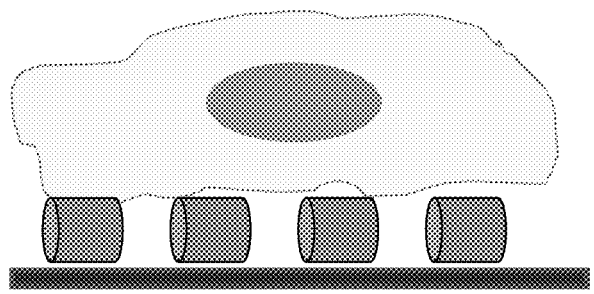
Figure 13:
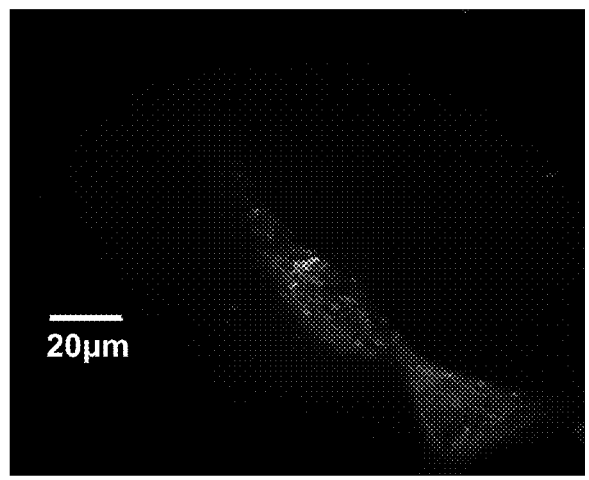

In one embodiment, the protrusions are located at the surface of the construct in a detachable or non-detachable form. Located in a detachable form means that the protrusions are not fixed to the surface. For example, in one embodiment protrusions, such as pillars are imprinted into the surface of the construct base material as described herein. After formation of the construct and the protrusions, such as pillars, the protrusions are disconnected from the surface of the construct by shearing. One specific example of this general process is illustrated in FIG. 12. This detaching allows for example to transfer the protrusions made of one material to a surface made of another material.

In one embodiment, the protrusions are pillars in the form of micropillars or nanopillars or in the form of a grating.

In one embodiment, the protrusions are cylindrical or polygonal. The polygonal protrusions may be triangular (3-sided), rectangular (4-sided), square (4-sided), pentagonal (5-sided), hexagonal (6-sided), 7-sided, 8-sided, 9-sided, 10-sided, 11-sided, 12-sided, 13-sided, 14-sided or 15-sided. The polygon may be equilateral or non-equilateral.

In one embodiment, the diameter or maximal width of the pillars may be in the nanoscale or microscale. The diameter of the pillars may be selected from the group consisting of between 10 nm to 5 µm, between 50 µm to 4 µm, between 200 nm to 2 µm, about 200 nm, about 300 nm, about 400 nm and about 500 nm.

In one embodiment, the diameter or maximal width of the pillars may be between about 200 nm to about 2 µm.

The aspect ratio (ratio between the width and height of the protrusion) may or may not be significant. For example, for PMMA, because of its high modulus, the aspect ratio of the topography does not play a significant role. However, when involving a low modulus polymer, the aspect ratio can affect the effective elastic modulus experience by the cells and altered its endocytosis uptake. A suitable range depends on the polymer use as it is linked to the fabrication limitation of the material. In some embodiments, an aspect ratio of 1:2 (width:height) was used for the 200 nm pillars and 1:1 was used for the 2 µm pillar and 250 nm grating. Thus, the aspect ratio can be between about 1:1 to 1:10 or between about 1:1 to 1:5 or between about 1:1 to 1:3 or it can be 1:1, 1:2, 1:3, 1:4 or 1:5.

In one embodiment, the gratings may have a width of between about 10 nm to about 2 µm, or between about 100 nm to about 1.5 µm.

In one embodiment, the pillars are extending substantially perpendicular from the surface of the construct or wherein the pillars are collapsed pillars lying at the surface of the construct; wherein in case the pillars are collapsed pillars they have a length of between about 50 nm to about 5 µm.

In one embodiment, the pillars of the grating are extending between about 50 nm to 4 µm, or between about 100 nm to about 2 µm above the surface of the construct.

In one embodiment the protrusions may be spaced apart from each other by between 200 nm to 12 µm, or 400 to 10 µm, or 5 nm to about 1 µm. In other words the "pitch" is equal to the center to center of 2 adjacent protrusions, such as pillars or gratings.

In one embodiment, the protrusions are micropillars and the pitch between the micropillars from an edge of one micropillar to an edge of another micropillar may be between 1 to 10 µm, or about 9.5 µm.

In one embodiment, the protrusions are nanopillars and the pitch between the nanopillars from an edge of one nanopillar to an edge of another nanopillar may be between 150 to 300 nm, or 200 nm to 250 nm.

In one embodiment, the pitch between the protrusions may be less than the size of the cells to be located at the surface of the construct.

In one embodiment, a residual layer may be arranged between the pillars and the surface of the construct. In one embodiment, the residual layer may be removed from between the pillars by reactive ion etching. The residual layer can be made of the same or different material than the pillars and/or the surface of the construct.

In one embodiment, the construct may be obtained via nano-imprinting lithography (NIL).

In one embodiment, the nano-imprinting lithography may be thermal nano-imprinting lithography or UV nano-imprinting lithography.

In one embodiment, the construct and/or the protrusions may be made of a polymer. In one embodiment, the polymer may be a synthetic polymer, or a rigid synthetic polymer, or a biodegradable polymer.

In one embodiment, the synthetic polymer may be selected from the group consisting of poly(methyl methacrylate) (PMMA), polydimethylsiloxane (PDMS), polystyrene (PS) and mixtures thereof.

In one embodiment, the biodegradable polymer include, but are not limited to of chitosan, poly($\epsilon$-caprolactone), polyglycolic acid, polylactic acid), polyphosphoester (PPE), poly(lactide-co-glycolide), poly(lactide-co-caprolactone), poly(glycolide-co-caprolactone), polydioxanone, polytrimethylenecarbonate, poly(glycolide-co-dioxanone), polyamideester, polypeptide, polyorthoesters, polymaleic acid, polyphosphazene, polyanhydride, polycebacicanhydride, polyhydroxyalkanoate, polyhydroxybutylate, polycyanoacrylate and mixtures thereof.

In one embodiment, a bioresorbable polymer is used. Examples of bioresorbable polymers include, but are not limited to a mixture of two or more bioresorbable homopolymers derived from the polymerization of alpha-hydroxy carboxylic acids, and a mixture of one or more bioresorbable terpolymers derived from the condensation of a dicarboxylic acid, an alpha hydroxy carboxylic acid and an aliphatic diol and one or more homopolymers derived from the polymerization of alpha-hydroxy carboxylic acids, said homopolymers and said terpolymers having an average molecular weight equal to or greater than about 150,000 as measured by gel permeation chromatography and wherein at least one of said homopolymers and said terpolymers has an average molecular weight of from about 234,000 to about 320,000 as measured by gel permeation chromatography. Other examples of bioresorbable polymers include, but are not limited to polyhydroxyalkanoates such as poly(hydroxybutyrate) (PHB), poly(hydroxyvalerate) (PHV) and poly(hydroxybutyrate-co-valerate) (PHBV), polylactones, such as polycaprolactone (PCL), poly(L-lactic acid) (PLA), poly (glycolic acid) (PGA), poly(lactide-co-glycolide) (PLGA), polydioxanone, polyorthoesters, polyanhydrides, poly(glycolic acid), poly(D,L-lactic acid), poly(lactide-co-caprolactone), poly(glycolic acid-co-trimethylene carbonate), polydioxanone, polyorthoesters, polyphosphoesters, polyphosphoester urethanes, polyanhydrides, poly(amino acids), polyacrylates, cyanoacrylates, poly(trimethylene carbonate), polyurethanes, poly(iminocarbonate), copoly(etheresters) (e.g. PEO/PLA), polyalkylene oxalates, polyphosphazenes and biomolecules, such as fibrin, fibrinogen, starch, collagen, hyaluronic acid, etc., other natural polymers such as alginate, polysaccharides such as dextran and cellulose, etc. and mixtures thereof.

in one embodiment, the rigid synthetic polymer may be polystyrene. In one embodiment, the polystyrene may be tissue-culture grade polystyrene (TCPS).

For manufacturing purposes or even after manufacturing the construct can be mounted or attached to another support surface, such as a metal surface. As illustrated for example in FIG. 12, the construct can be attached to a semiconductor surface, such as a silicon surface.

In one embodiment, during manufacture of the construct, the polymer may be mixed with molecules which are to be absorbed by the cell to be located on the construct. In another embodiment, the molecules may be attached to the surface of the protrusions. The molecule may be immobilized via chemical bonding or adsorbed on the surface of the protrusion, wherein adsorption does not involve chemical binding.

In one embodiment, the cell comprising cell types comprising an apical membrane or cell types comprising a basolateral membrane.

In yet another embodiment, a method of promoting absorption of molecules by cells is disclosed. The method comprises:
    providing a construct as defined above;
    seeding and culturing at least one cell at the surface of the construct under conditions suitable for absorption of molecules by the cells.

In one embodiment, the absorption of molecules is via endocytosis, or pinocytosis, or phagocytosis.

In another embodiment, absorption of the molecules may be via a non-viral carrier or a viral carrier. This is advantageous as non-viral vectors do not trigger an immune response and may be delivered by processes including but not limited to endocytosis. Examples of non-viral vectors include nano-particles and liposomes. In one embodiment, the viral carrier may be a virus that is used to deliver material into cells. Examples of suitable viral vectors include retroviruses, lentiviruses, adenoviruses and adeno-associated viruses.

In one embodiment, the molecules to be absorbed may be selected from the group consisting of nucleic acid, nucleic acid vectors, siRNA, microRNA, magnetic nanoparticles, gold nanoparticles, fluorescent nanoparticles, quantum dots, aptamers (oligonucleic acid or peptide), peptides, growth factors, therapeutically active substances, biomarkers, colouring agents, and any one of the aforementioned molecules attached to a microparticles.

In one embodiment, a method of cell transfection, or drug-delivery or high-throughput screening arrays using a construct is defined above is disclosed.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings Wing within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Example 1

This example demonstrates the verification of topographical structures on the substrate.
Material and Methods
Fabrication of Upright-Patterned Structures
Patterned substrates were fabricated using nanoimprint lithography as previously documented. Briefly poly(methyl methacrylate) (PMMA) (Microresist, PMMA, MIA/35000 g/mol) was first spin-coated on a clean silicon substrate to form a thin PMMA film before a silanized silicon mold was placed on top of the spin-coated surface and the imprinting was carried out at 150° C. under a pressure of 60 bar for 10 minutes. Subsequently, the system was cooled before demolding the silicon master from the imprinted PMMA polymer layer. The fabricated upright PS pillar structures can also be collapsed and collected using a polydimethylsiloxane (PDMS) slab, hence forming an ordered array of detachable structures. All structures used in the study to be described in the following were fabricated using PMMA except for collapsed pillar structures.
Fabrication of Residual Free Pillar Structures
Upright PMMA pillars were fabricated as described above with an addition of Rhodamine B (Sigma-Aldrich, Rhodamine 11.0 chloride, $M_w$ 366.8 g/mol). Subsequently, a reactive ion etching machine (Plasmalab 80plus, Oxford) was used to remove the residual layer of the imprinted substrate.
Verification of the Imprinted Structure by Scanning Electron Microscope (SEM)
The fidelity of imprinted structures was verified using a SEM (JEOL, JSM-6700F). Samples were coated for 20 seconds using a gold coating machine (JEOL, JFC-1200) to achieve a gold film thickness of approximately 10 nm. The structures were viewed using an accelerating voltage of 5 kV, at a working distance of 6 mm.
Results
Scanning electron microscopy (SEM) was used to verify the micro and nano structures formed on the substrate after nano-imprint lithography. For the PMMA upright structures with residual layer, 3 structures were used, 2 µm pillars, 200 nm pillars and 250 µm gratings. For the residual layer free PMMA upright structures, 200 nm pillars were used. For the polystyrene (PS) collapsed pillars, 2 µm pillars were used. FIGS. 1A-C and FIGS. 1D-E show the top and cross sectional SEM images of the various structures fabricated for the experiments respectively, while FIG. 1F shows the top view SEM image of the collapsed detachable pillars.
These results indicate that all SEM images showed high fidelity and dimensions that were in accordance with the initial mold used.

Example 2

Figure 2:
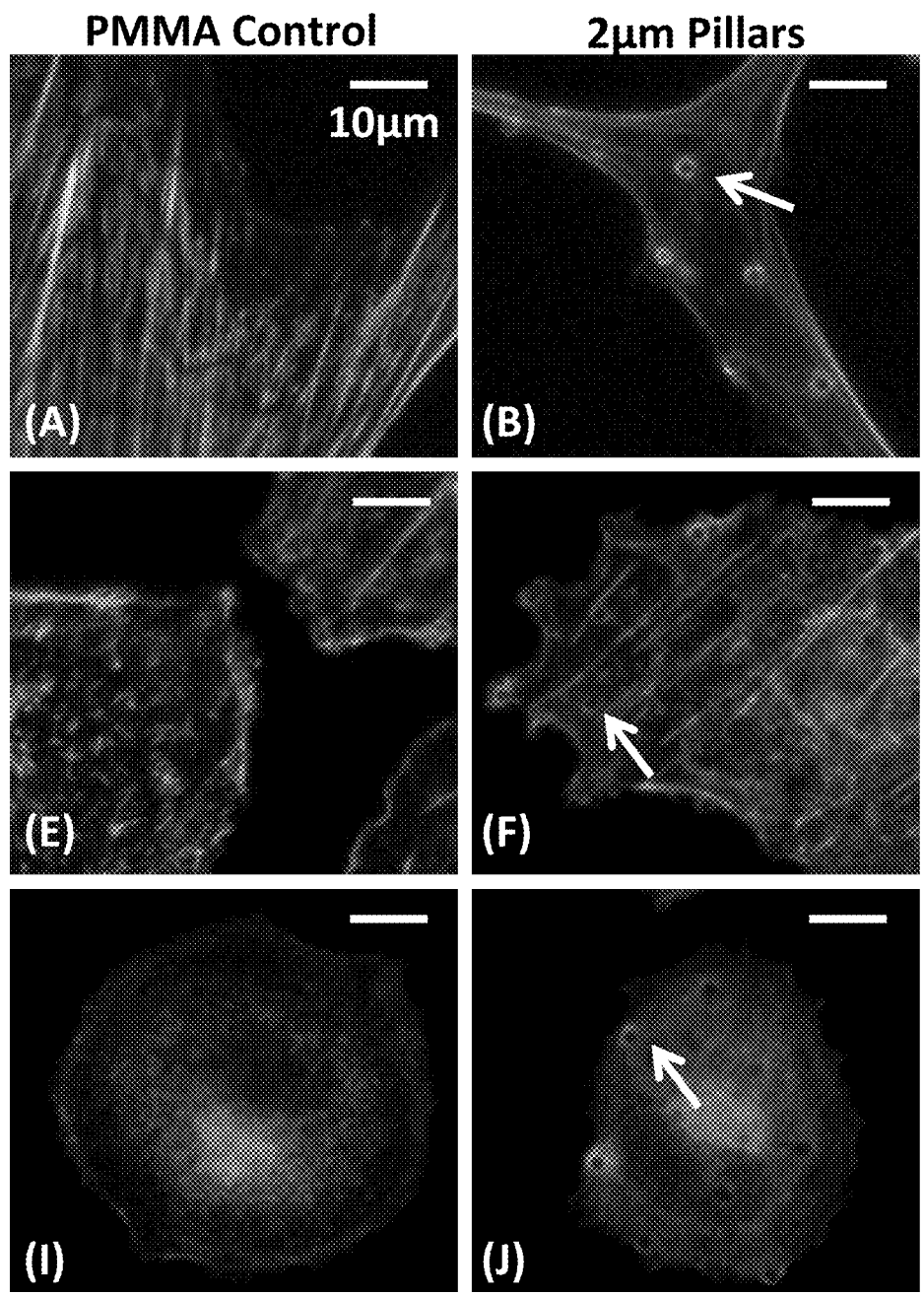
FIG. 2 shows magnified images of fluorescently stained F-actin (red—bright colour) hMSC (A-D), COS7 (E-H) and MCF7 (I-L) cultured on PMMA control, 2 μm pillars, 200 nm pillars and 250 nm gratings, respectively. It can be seen from FIG. 2 that actin-dense ring regions coincide with the underlying pillar topography on the micron sized structures as indicated by the white arrows while they were also faintly observed in the nanopillar substrates. It can also be observed that F-actin in 250 nm gratings were aligned and elongated to the grating axis (indicated by the double ended arrows). (White bars=10 μm)
Figure 2:
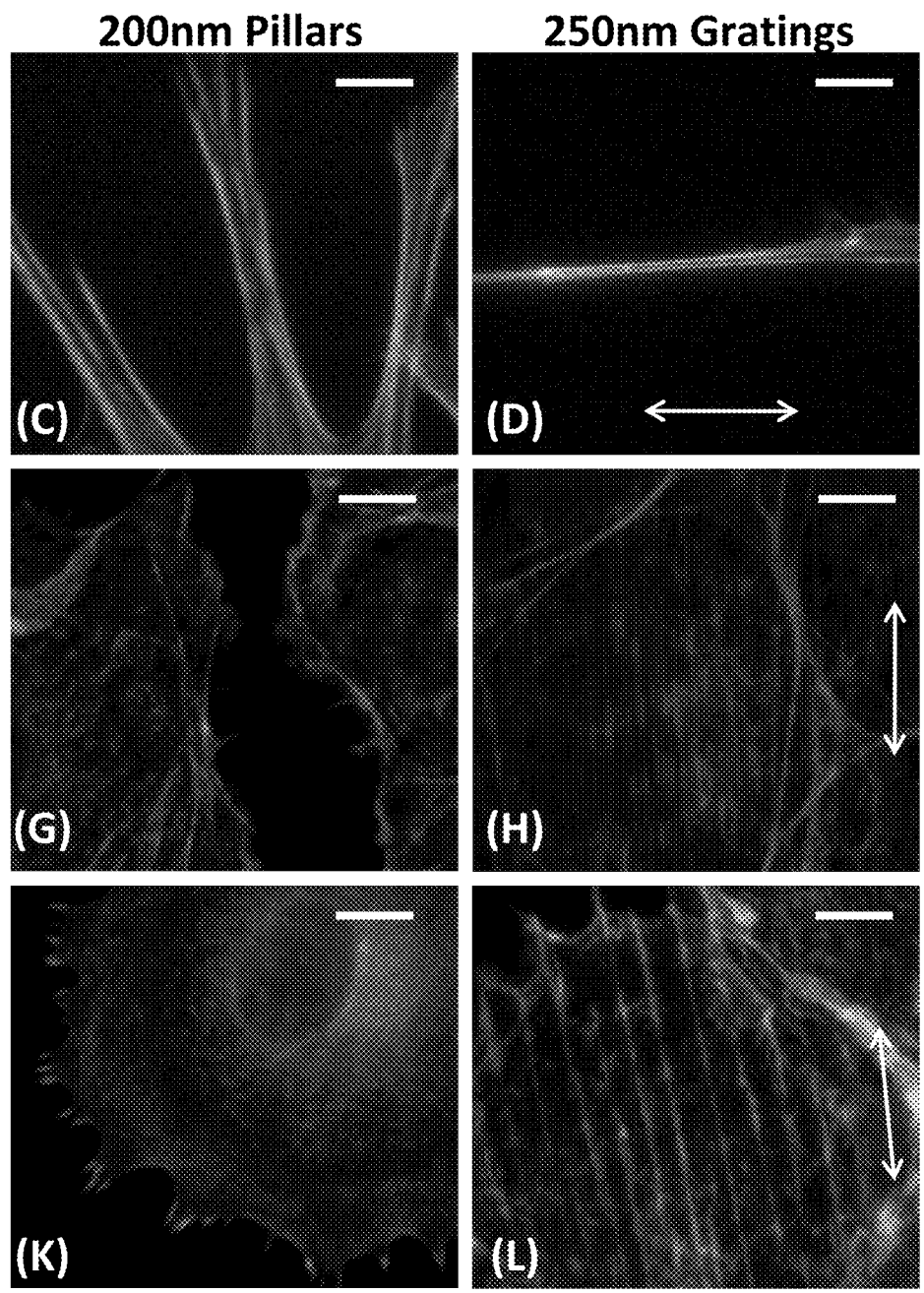
Figure 9:
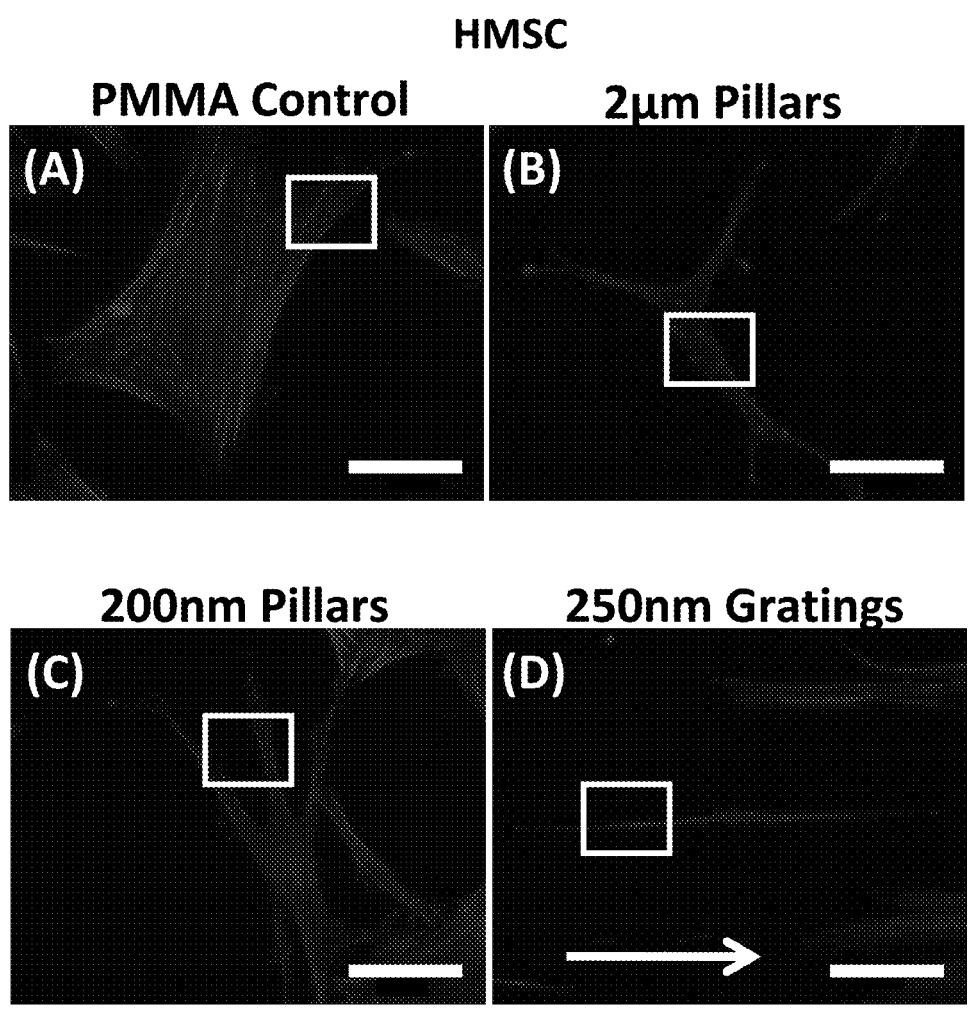
FIG. 9 shows fluorescent images of human mesenchymal stem cells (hMSCs), COS7 and MCF7 cells on unpatterned (A, E and I), 2 µm pillars (B, F and J), 200 nm pillars (C, G and K), 250 nm gratings PMMA substrates (D, H and L) 24 hours after cell seeding respectively. Cells were stained for F-actin using Alexa Fluor 546 Phalloidin (bright colour) and counterstained with DAPI (circles with dotted line). Arrows indicate the direction of nanogratings while White boxes indicate the region magnified for easier visualization (shown in FIG. 2). (Bars=50 µm). It can be seen from FIG. 9 that generally cells are more spread out on unpatterned and pillar substrates as compared to grating substrates where they exhibit an elongated morphology.
Figure 9:
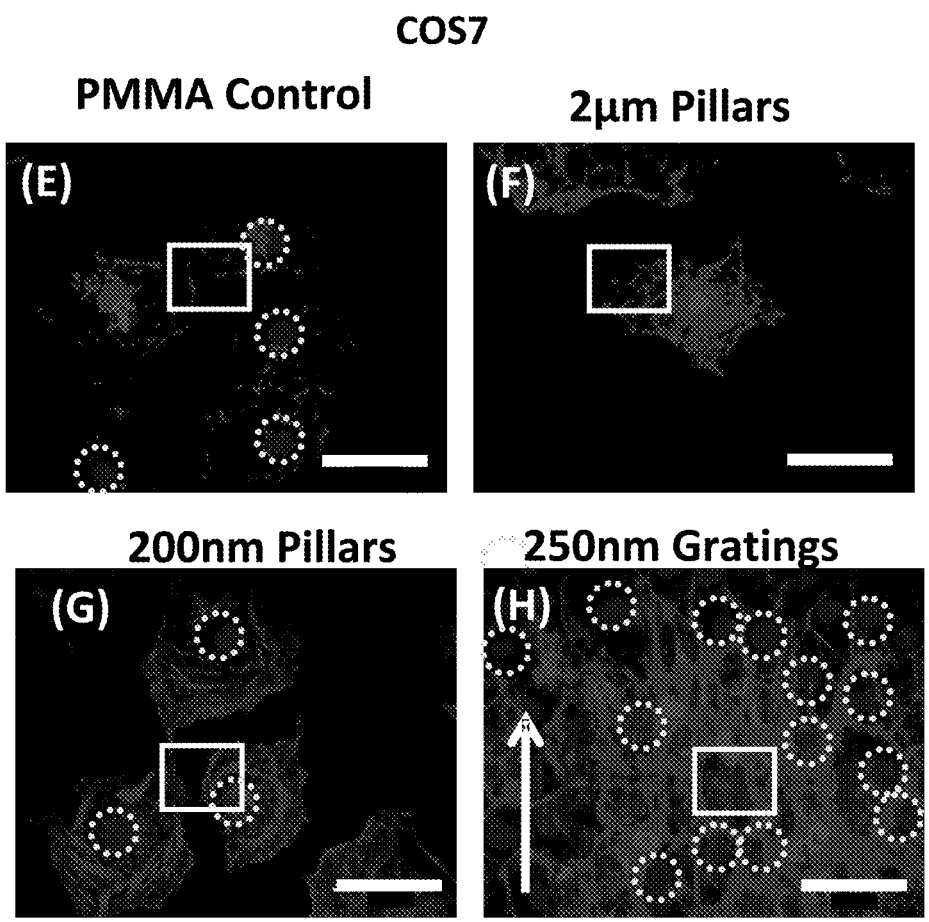
Figure 9:
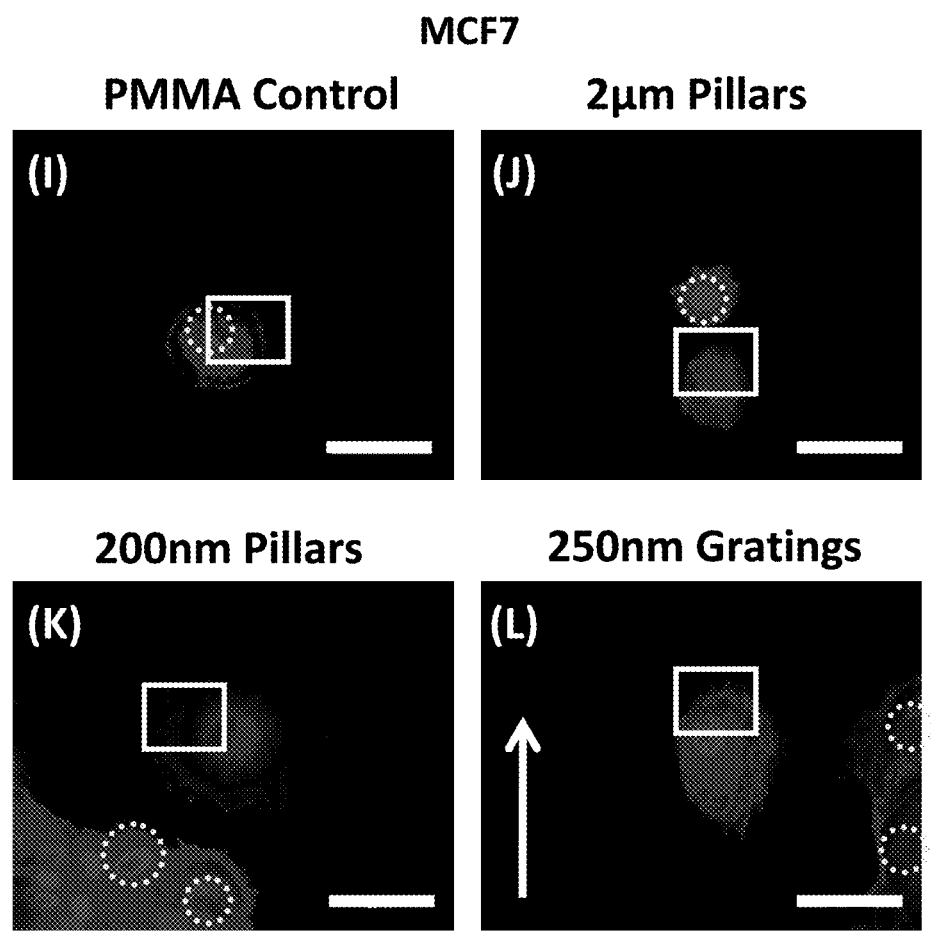

This example demonstrates fluorescence imaging of cellular morphologies on different topographies.
Materials and Methods
Cell Culture
Bone marrow human mesenchymal stem cells (hMSCs) (CD105+, CD166+, CD29+, CD44+, CD14−, CD34−, CD45−, Lonza, Poietics) were cultured and expanded in serum containing Mesenchymal Stem Cell Growth Medium (MSCGM, Lonza) according to the manufacturer's protocol. The hMSCs used for experiments were at passages 5-7.
MCF7 breast cancer cells (ATCC) were cultured in Eagle Minimum Essential Medium (Sigma) containing 10% fetal bovine serum (Gibco, Invitrogen), 1% Penicillin-Streptomycin (Gibco, Invitrogen) and 0.01 mg/ml bovine insulin (Sigma). COS7 fibroblasts (ATCC) were cultured in a medium containing DMEM (Gibco, Invitrogen), 10% fetal bovine serum and 1% Penicillin-Streptomycin (Gibco, invitrogen).
Topographical substrates were first sterilized under ultraviolet light for 20 minutes, before respective cells were seeded at 10,000 cells/cm$^2$ in a 6-well tissue culture plate. Collapsed PS pillars on PDMS substrates were rinsed with 70% ethanol before being air dried and subsequently seeded with hMSCs at 5,000 cells/cm$^2$.
Fluorescence Imaging of Cell Morphology on Topographies
Cells cultured on different substrates were stained for F-actin using AlexaFluor 546 Phalloidin and counterstained with 4',6-diamidino-2-phenylindole (DAPI, Sigma-Aldrich). Briefly, cells were fixed in 4% PFA in PBS before cell permeabilization using 1% Triton-X-100 in PBS for 15 minutes. The samples were then incubated with 1:750 Alexa Fluor 546 Phalloidin (Molecular Probes, invitrogen) and 1:2500 DAPI for twenty minutes before mounting. Samples were observed and imaged using a fluorescence microscope (Leica epifluorescence microscope Leica DM IRB). For visualization of dextran internalization, FITC-dextran (lysine fixable, Molecular Probes) at 1 mg/ml was added to the culture medium before cells were fixed for F-actin staining after 24 hours.
Results
Fluorescently labeled hMSCs, COS7 and MCF7 cells showed characteristic morphologies on the various topographies after 24 hours (FIG. 2). Generally, cells were more spread out on unpatterned and pillar substrates as compared to grating substrates where they exhibited an elongated morphology (FIG. 9). F-actin stress fibers showed the different distribution of the actin cytoskeleton on these topographies. Cells that were cultured on the 2 µm pillars showed intracellular actin rich rings that outlined the top surface of the upright pillar substrates the cells were in contact with (FIG. 2). The actin rich regions were of a higher intensity in the micron sized pillars compared to the nano-sized pillars while no such actin rich regions were seen on the grating topography. Stress fibers on these cells bridged these actin rich regions, seemingly connecting these rings together in a web like fashion while cells that were cultured on the 250 nm gratings substrate showed a distribution of stress fibers that were aligned to the grating axis.
Accordingly, these results show that morphological changes are closely linked to cellular adhesions, the focal adhesions, that have an intertwined regulation with actin cytoskeleton.

Example 3

This example demonstrates the effect of topographical structures on apical FITC dextran internalization.
Materials and Methods
Internalization of FITC-Dextran
Respective cells were cultured on various patterned substrates for 24 hours before fluorescein isothiocyanate (FITC)-dextran molecule (Sigma Aldrich, MW 40,000) was added to all samples at a concentration of 1 mg/ml with the exception of the positive control where a higher concentration of 2 mg/ml was added to cells cultured on unpatterned PMMA substrates. At the specific time points of interest, the cells were detached for subsequent flow cytometry analysis. For the comparison study between two FITC-dextrans of different molecular weights, the experiment was similarly carried out using an additional type of FITC-dextran with higher molecular weight (Sigma Aldrich, MW 500,000).

Flow Cytometry Analysis of Internalized Dextran in Cells

For FITC-dextran internalization studies, patterned substrates containing the cells were rinsed with phosphate buffered saline (PBS) solution and subsequently detached from the substrate using trypsin-EDTA for COS7 and MCF7 while Accutase (Stem Cell Technologies) was used for hMSCs. The appropriate medium was then added to neutralize the enzymatic detachment process before the cells were washed, re-suspended in PBS and fixed in 0.5% paraformaldehye (PFA). Cells were passed through a 60 µm pore size nylon filter before analyzing using a Dako flow cytometry Analyzer (Dako Cytomation Cyan LX). Cells cultured in the absence of FITC-dextran were used as the gating and negative controls where a minimum of 10,000 events were recorded for each of the triplicate samples.

Statistics

For comparisons of internalization efficiency between different topography and control, one-way ANOVA analysis was performed before Bonferroni's Multiple Comparison Tests were carried out between different topographies and control, with a p-value of at least <0.05 considered as significant. Errors bars denote the standard deviation of at least 2 independent experiments. In flow cytometry analysis of FITC dextran and GFP transfection, the percentage of fluorescence population and mean fluorescence intensity was studied.

Results

Flow cytometry analysis was carried out to investigate the effect of topographical cues on the uptake of FITC-dextran mainly from the apical surface of the cell membrane. The three different cell types used in this study were COS7, MCF7 and hMSCs, representing fibroblastic cells, cancer cells and multipotent stem cells respectively.

Effect of Topography and FITC-Dextran Molecular Weight on COS7 Internalization

Figure 3A:
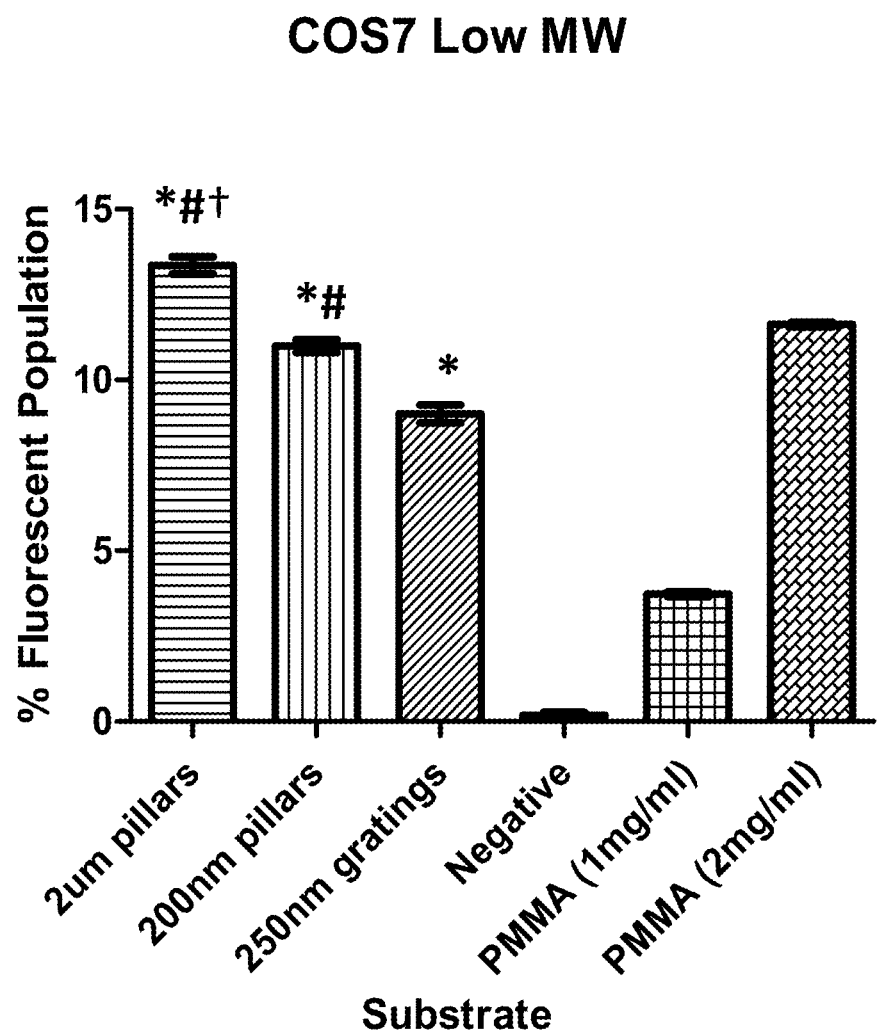
FIG. 3A shows the overall percentage of fluorescent population of COS 7 on 2 μm pillars, 200 nm pillars, 250 nm gratings and PMMA control, where 1 mg/ml of FITC-dextran (low MW) was added. (P<0.01 *-vs control 1 mg/ml, #-vs 200 nm gratings, †-vs from 200 nm pillars, n=3).

FIG. 3 shows the fluorescent population of COS7 cells when they were cultured on different topographies in FITC-dextran containing medium for 24 hours. In FIG. 3A, COS 7 cells seeded on 2 µm pillar (13.36±0.44%), 200 nm pillar (10.99±0.33%) and 250 nm grating (9.01±0.45%) had a significantly larger fluorescent population compared to the PMMA unpatterned control (4.5%).

Comparing between the topographies, 2 µm pillars were also significantly different from 200 nm pillars and 250 nm gratings, inducing the largest increase in FITC-dextran uptake among the topographies tested while 250 nm gratings showed the least increase in FITC-dextran uptake compared to an unpatterned surface. The FITC-dextran used in this experiment was of a relatively lower molecular weight (40,000) compared to FIG. 3B.

Figure 3B:
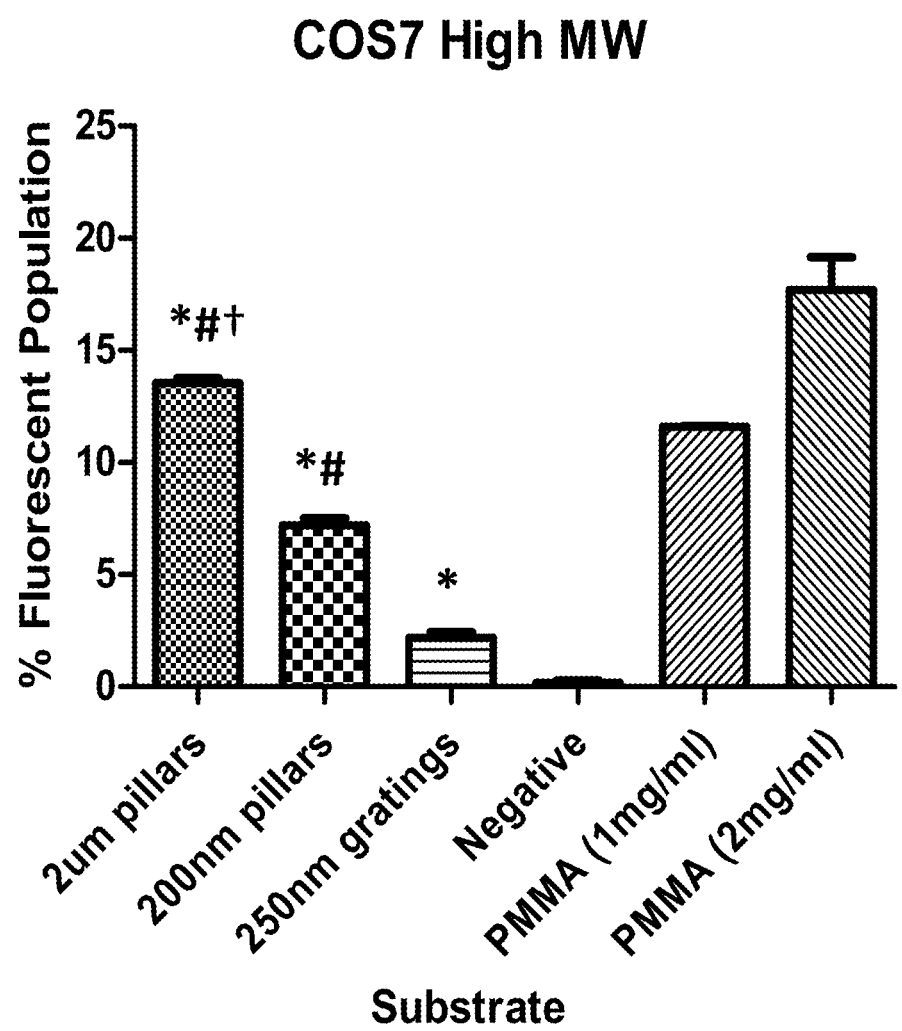
FIG. 3B shows the overall percentage of fluorescent population of COS 7 on 2 μm pillars, 200 nm pillars, 250 nm gratings and PMMA controls, where 1 mg/ml of FITC-dextran (high MW) was added. (P<0.01, *-vs control 1 mg/ml, #-vs 200 nm gratings, †-vs 200 nm pillars, n=3). An independent PMMA control with 2 mg/ml of FITC-dextran was carried out as the positive control in both FIGS. 3A and 3B. It can be seen from FIG. 3 that the observed trend of dextran intake among the topographical patterns is similar for the different molecular weights.

A similar experiment was carried out using a higher molecular weight of FITC-dextran molecule (500,000) as shown in FIG. 3B. Using a higher molecular weight FITC-dextran resulted in a general decrease in fluorescent population across all substrates except for the 2 in pillars (13.56±0.33% vs. 13.36±0.44%). All other topographies showed a decrease in fluorescent population (high MW vs. low MW), 200 nm pillars (7.20±0.42% vs. 10.99±0.33%), 250 nm gratings (2.18±0.36% vs. 9.01±0.45%). The generic decrease in higher molecular weight FITC-dextran uptake, however, did not affect the trends observed among the different topographies, 2 µm pillars similarly induced the highest amount of FITC-dextran internalization while 250 nm gratings were the least. When 200 nm pillars and 250 nm gratings were compared to the unpatterned control substrate, the fluorescent population was significantly lower while the 2 µm pillars remained significantly higher.

Effect of Topography on MCF7 FITC-Dextran Internalization

Figure 4:
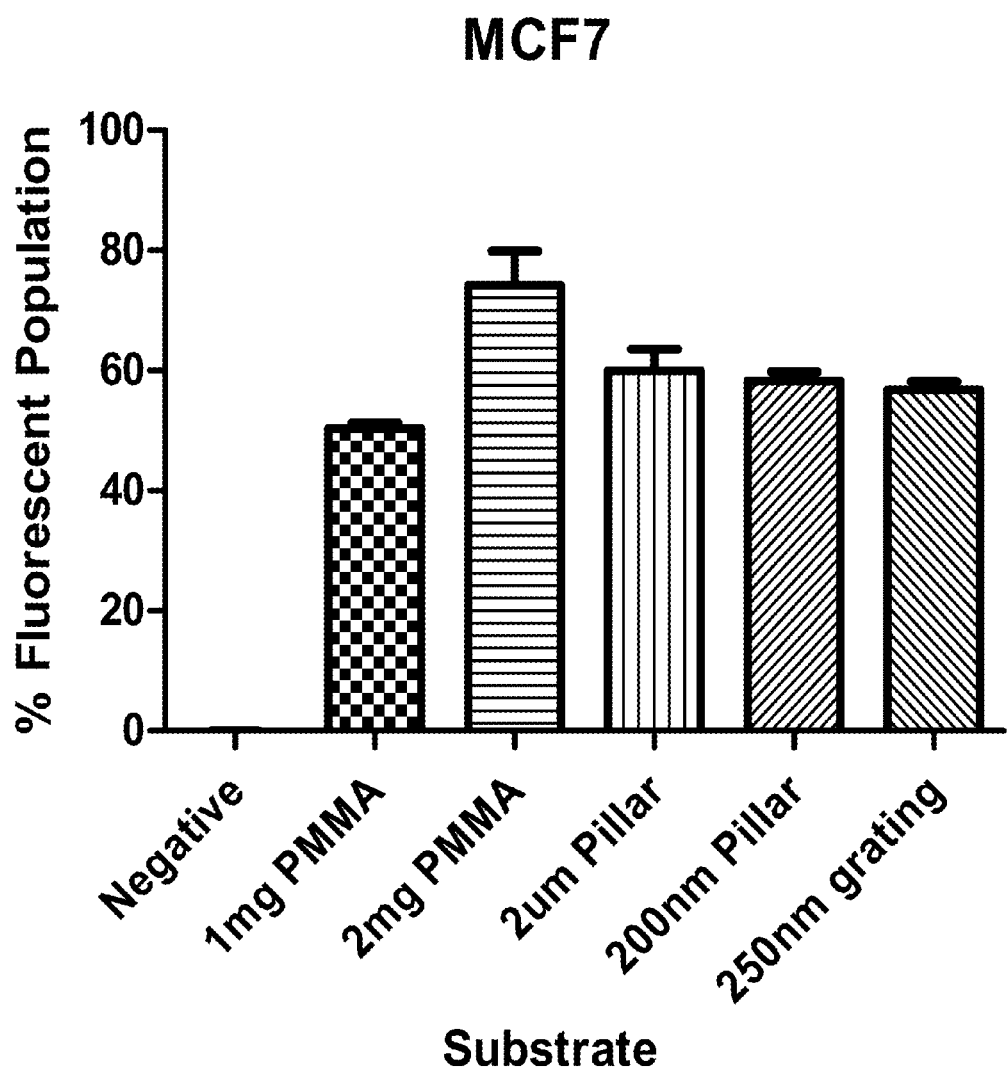
FIG. 4 shows the flow cytometry analysis of FITC-dextran internalization in MCF 7 breast cancer cells cultured on 2 μm pillars, 200 nm pillars and 250 nm gratings with PMMA control (2 mg/ml) after 24 hours of incubation time. It can be seen from FIG. 4 that no statistical difference was observed amongst the different topographies in the breast cancer cell population.
Figure 5A:
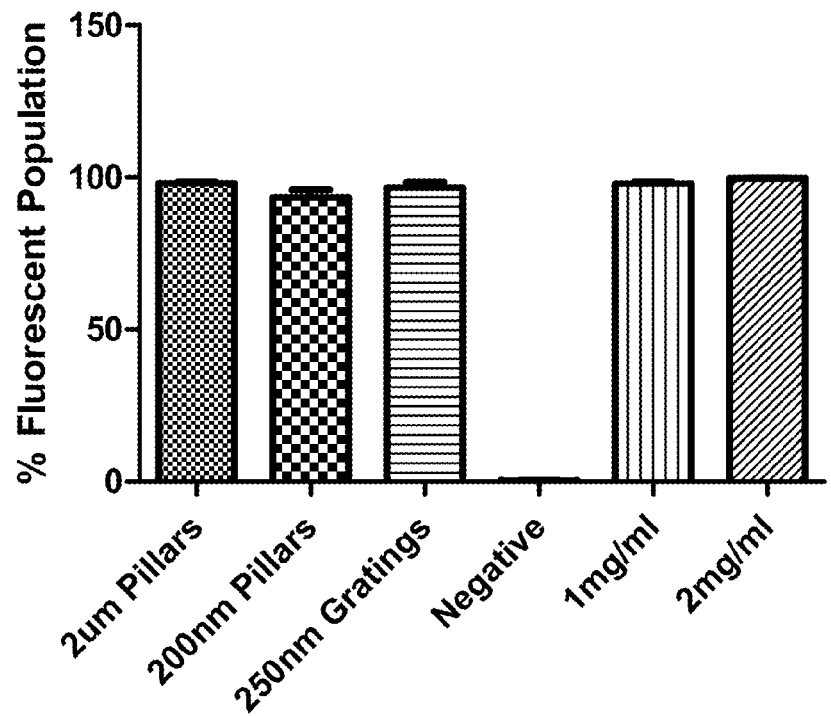
FIG. 5 comprises FIG. 5A to 5D and shows the flow cytometry analysis of FITC-dextran internalization in hMSC cultured on 2 µm pillars, 200 nm pillars, 250 nm grating and PMMA control (1 mg/ml). PMMA control (2 mg/ml) represents the positive control for the experiment. The percentage of fluorescent hMSC population was analyzed at 18 hours (FIG. 5A), 6 hours (FIG. 5B), 3 hours (FIG. 5C) and 2 hours (FIG. 5D) of incubation time. It can be seen from FIG. 5 that hMSCs that were cultured on 2 µm pillars after 3 hours of incubation time showed significantly increased dextran internalization compared to 200 nm pillars, 250 nm gratings and PMMA control. ($P<0.01$ *-vs control 1 mg/ml, #-vs 250 nm gratings, †-vs 200 nm pillars, n=3).
Figure 5B:
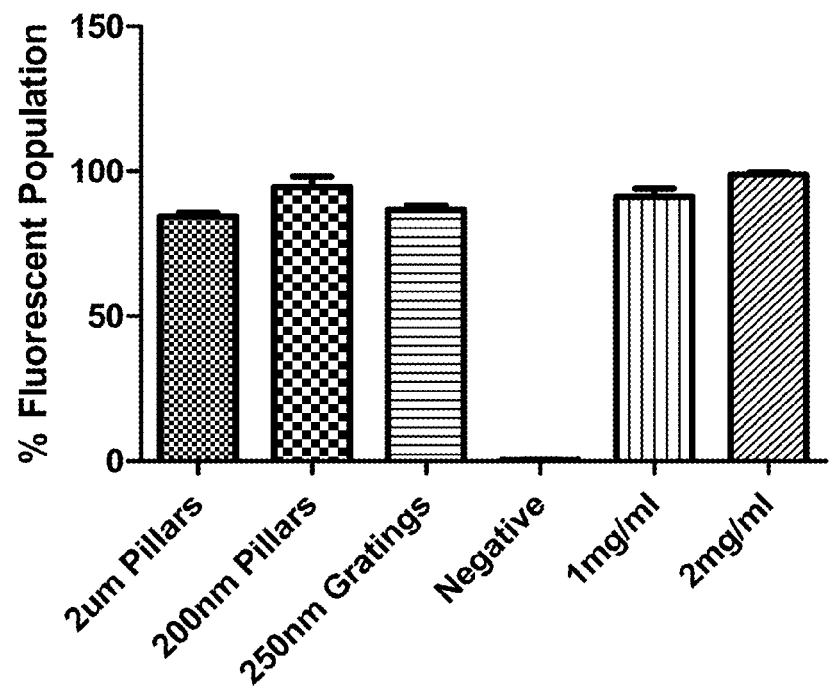
Figure 5C:
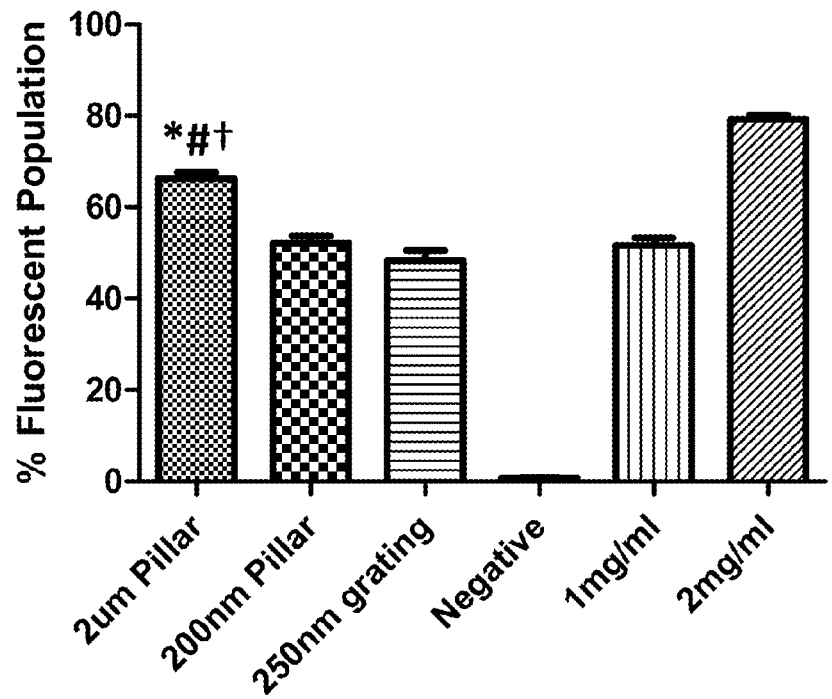
Figure 5D:
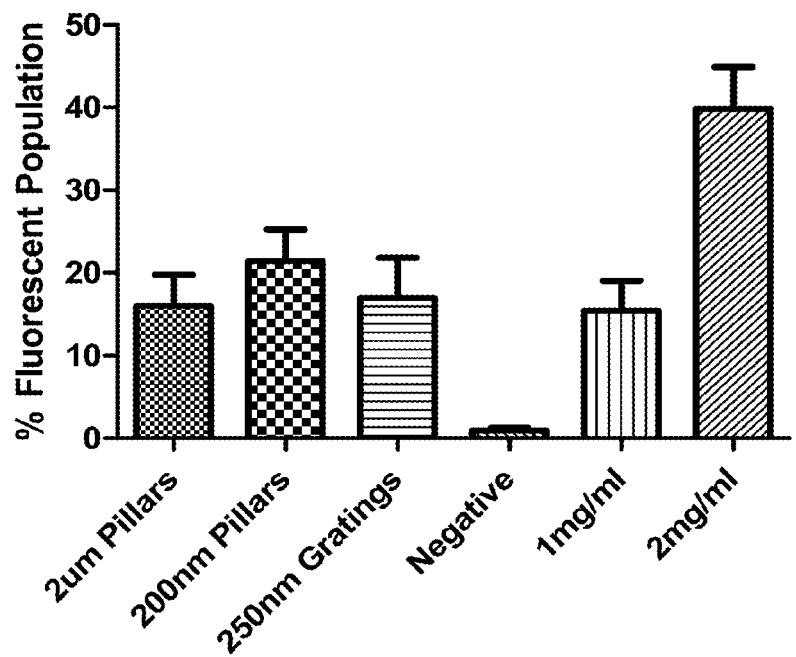

Results from a repeat experiment using MCF7 are shown in FIG. 4. MCF7 on 2 µm pillars (59.99±7.98%), 200 nm pillars (58.28±4.02%) and 250 nm gratings (56.78±3.10%) did not show any significant difference in the fluorescent population when cultured on these topographies compared to the unpatterned PMMA control (50.35±1.68%).

Effect of Topography and Incubation Time on hMSC FITC-Dextran Internalization

The results for similar experiments performed using hMSCs are shown in FIG. 5. In addition to a 24 hour time point (data not shown) as previously used for both COS7 and MCF7 cells, the experiments were carried out at different cell incubation times in FITC-dextran containing medium. FIG. 5 shows the results obtained for the fluorescent population of hMSCs on different topographies at incubation times of 18 hours (FIG. 5A), 6 hours (FIG. 5B), 3 hours (FIG. 5C) and 1 hour (FIG. 5D) respectively. Results from FIGS. 5A and 5B showed the saturation of FITC-dextran internalization where hMSCs cultured on the different topographies all showed a similar absolute population fluorescence at 18 hours (2 µm pillars: 98.01±1.35%, 200 nm pillars: 93.45±5.66%, 250 nm gratings: 96.64±3.64%). Results obtained for the 6 hour time point was similar to the fluorescent population on 2 µm pillars at 84.43±1.77%, 200 nm pillars at 94.55±6.34% and 250 µm gratings at 86.73±1.99%. These results demonstrated that the uptake of FITC-dextran was saturated at these time points with the specified FITC-dextran concentration in medium.

When the analysis was carried out after 3 hours of FITC dextran incubation, the 2 µm pillar showed a significantly higher percentage of fluorescent population (P<0.01) as compared to the control (1 mg/ml), 250 nm grating and 200 nm grating, similar to earlier observations in COS7 cells. When the same analysis was carried out at the 1 hour time point, the percentage of fluorescent hMSCs on 2 µm pillars (16.02±8.38%), 200 µm pillars (21.44±9.37%) and 250 µm gratings (16.97±10.88%) were higher than the unpatterned control (15.41±8.12%) although these differences were not statistically significant.

Accordingly the enhanced internalization of FITC-dextran in COS7 and hMSCs on 2 µm pillars show that micron sized topography is able to increase the pinocytosis rate of cells cultured on these patterned substrates.

Macropinocytosis is initiated from actin-rich regions of the plasma membrane called ruffles that are closely coordinated by actin and its key regulators, the family of Rho GTPases (Rho, Cdc42, Rac). In hMSCs and COS 7 on both the micron and nano sized pillar substrates (FIG. 2), intracellular rich actin rings were observed residing on the top surface of the pillars, with the micron sized pillars showing actin rings which were larger and of a higher fluorescence intensity. Micron sized pillars were able to induce more actin dense regions in hMSCs and COS7 compared to the nano pillars and gratings, changing the intracellular contractility and upregulating RhoGTPases to enhance ruffling and thus macropinocytosis. Indeed, results from the FITC-dextran experiment demonstrated that 2 µm sized pillars induced the strongest enhancement in macropinocytosis rate in both COS7 and hMSC. Similarly, lesser such actin-dense regions observed in MCF7 corresponded to an insignifcant difference in FITC-dextran internalization when the MCF7 cells were cultured on the different topographical patterns. This can also be due to the increased ruffling in MCF7 metastatic cells compared to the other cell lines, masking the effect of topography on macropinocytosis since cancer cells often exhibit increased motility.

On the other hand, the hMSCs that were cultured on different substrate topographies exhibited different integrin subunits profiles, suggesting different integrin trafficking rates in hMSCs on different topographies. Cell migration requires integrins to be redistributed from disassembling focal adhesions to new assembling focal adhesions at the leading edges and the initial step of integrin redistribution has been shown to involve clathrin-mediated endocytosis of β-1 integrins. Cell stimulation using platelet-derived growth factor for cell migration also causes a rapid redistribution of integrins to the dorsal circular ruffles before being internalized through macropinocytosis.

The increased rates of macropinocytosis in the examples may be a synchronized result of increased integrin transport on micron sized topography. Cellular migrations are generally lower on gratings compared to pillar substrates while the micron size pillar substrates are more widely spaced apart compared to the dense nano-sized pillars patterns which gives difficulty for cells to find a suitable path for attachment and thus migration, exhibiting slower motility in these nanopillar substrates.

Accordingly, topography like growth factors, can be a potent stimulus for cellular migration, exhibiting differential cell migration rates on different substrate topographies.

It is also interesting to note that hMSCs on different topographies adopted morphology that had vastly different surface area, with the largest being on the unpatterned control. These results suggest that the effect of topography on macropinoctyosis is independent of the surface area of contact with cargo FITC-dextran. In addition, the results of employing two different molecular weight of FITC dextran tracers (MW 40000 versus 500000) suggests that the topographical effects on the macropinocytosis were only partly dependent on the conformation and size of cargo, with a decrease in the fluorescence population yet still observing a similar trend.

Results from the time point study suggest that topographical effects on the FITC-dextran internalization in hMSCs is the most apparent after 3 hours of incubation in dextran-1.5 containing medium as the dextran-internalization process seemed to be saturated after 6 and 18 hours of incubation, while 1 hour was insufficient to distinguish a significant difference between the patterned and unpatterned substrates. The results also indicate that topographical effects can only be observed at earlier time points before a steady-state of internationalization is reached.

Application of topography to increase the cellular uptake of naked DNA or drug-containing nanoparticles have the potential to make these macropinocytosis-depedent processes more efficient. Based on our results, we demonstrate that micro-structures enhance cellular internalization by the macropinocytosis pathway.

Example 4

This example demonstrates the effect of topographical structures on non-viral GFP transfection of hMSCs.
Materials and Methods
Green Fluorescence Protein (GFP) Plasmid Amplification
Pmax FP-Green-C vector (Lonza, 4.7 kb) which expressed maxFP-Green in mammalian cells were amplified in
*Escherichia coli* DH5α and purified using an AxyPrep plasmid midiprep kit (Axygen Bioscience). GFP plasmid was obtained in elution buffer and its concentration was measured at the absorbance wavelength of 260 nm (Nanodrop 2000, Thermo Scientific).

Transfection of Bone Marrow Human Mesenchymal Stem Cells (hMSC) on Topographies
The transfection experiment was carried out similar to the FITC-dextran internalization study. 24 hours after seeding hMSCs on substrates placed in a 6 well plate, the cells were transfected with GFP plasmid using Lipofectamine 2000 (Invitrogen) reagent volume (µl) to GFP plasmid mass (µg) at a ratio of 1:2.5 in Opti-MEM (Invitrogen). After 3 hours of incubation, the transfection medium was replaced by fresh MSCGM medium with serum. The hMSCs were detached for flow cytometry analysis 18 hours after transfection, to allow time for GFP to be expressed.

Flow Cytometry Analysis of Non-Viral GFP Transfection of hMSCs
For transfection efficiency studies, hMSCs were similarly detached with Accutase, neutralized with MSCGM and washed with PBS. In order to determine cell viability, the Live/Dead cells stain (Invitrogen, Molecular Probes) was used according to the supplier's instructions. Cells were analyzed by flow cytometry as described above. Non-transfected cells were used as the negative control. Cells that stained positive for both GFP and Live/Dead assay were used as positive controls, while dead cells were used as negative controls to set the compensation for the individual populations.

Figure 6:
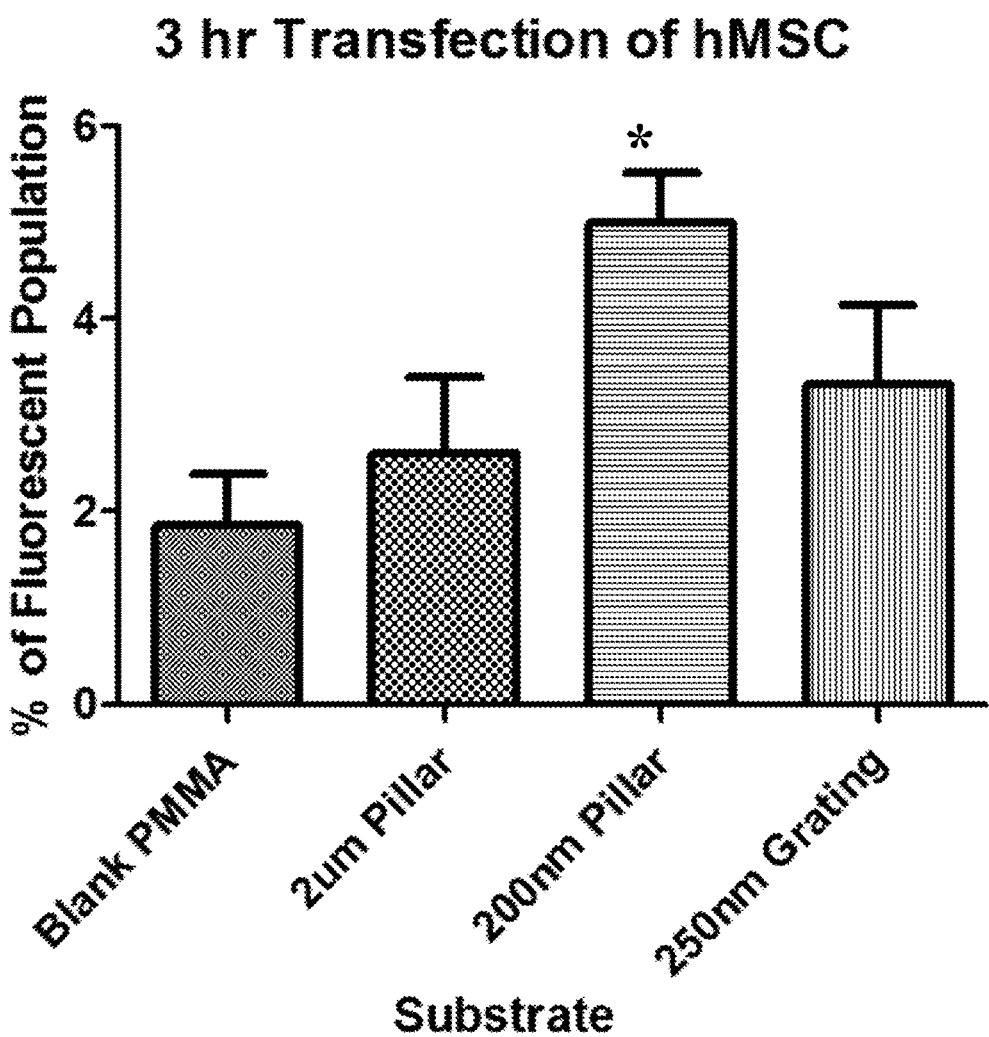
FIG. 6 shows the flow cytometry analysis of hMSCs cultured on 2 µm pillars, 200 nm pillars, 250 nm grating and blank PMMA control that were transfected for 3 hr with the GFP plasmid with the aid of lipofectamine 2000. It can be seen from FIG. 6 that there is a statistical difference in the percentage of fluorescence between cells cultured on the 200 nm pillars compared to PMMA control. ($P<0.05$, *-vs PMMA control, n=5).

Results
Flow cytometry analysis of Lipofectamine aided GFP transfection of hMSCs is shown in FIG. 6. Human MSCs cultured on unpatterned PMMA showed a mean fluorescent population of 1.8±1.18%. When hMSCs were transfected while attached to various topographical structures, an increase in the fluorescent population was observed. The hMSCs cultured on 2 µm pillars, 200 nm pillars and 250 nm gratings show a mean value of 2.60±1.8%, 5.00±1.16% and 3.32±1.83%, respectively (FIG. 6). Comparison between the three different topographies indicate that 200 nm pillars showed a 2.5 fold significant increase ($p<0.05$) in fluorescent population compared to blank PMMA.

This example inventigates the effect of GFP (+) transfection in hMSCs using both micron and nano-sized topography. Human MSCs are known to be highly sensitive and notoroiously difficult to transfect, causing research groups to resort to electroporation for enhanced transfection efficiency, although often at the expense of increased cell death. Cellular uptake of lipofectamine-mediated GFP plasmid occurs mainly by clathrin-mediated endocytosis, distinctively different from the earlier experiments targeted at macropinocytosis.

The amount of protein binding onto surfaces depends on the surface energy and exposed surface area. Nanoscale topography is able to significantly influence both the amount and the conformation of these adsorbed proteins. Substrate topography provides a 3-dimensional surface area for the adsorption of proteins while nanoscale topography further enhances the surface areas. Such differences in protein adsorption can have implications for cells, which exhibit intrinsic ability to sense minute-scale physical differences in the extra-cellular matrices.

However, the results suggest that surface area is unlikely to play an important role in the direct modulation of both macropinocytosis and clathrin-mediated pathway (FIG. 9) since surface area of the cells are largest on the unpatterned control.

Adherent cells respond to their surrounding microenvironment through the modeling of focal adhesions, which are also used in cellular motility. These focal adhesions can be modulated using substrate topography and the size of focal adhesions are a reflection of the state of intracellular actin-contractility.

hMSCs that were cultured on nanometer gratings showed reduced vinculin expression compared to unpatterned control, indicating a decreased actin cytoskeletal contractility on such topographical surface.

Actin cytoskeletal tension plays an important role in regulating endocytosis related proteins including integrins, clathrin and caveolin-1. The results show that the use of topography allows the modulation of cytoskeletal arrangement within the cell, in turn regulating the plasma membrane tension which changes the cell endocytosis rate.

The results also show that hMSCs on nanosized structures have a higher affiliation to the receptor-mediated endocytosis; caveolae-mediated encytosis and clathrin-mediated endocytosis.

Without being bound by any specific theory, we consider that nanotopography can increase hMSCs transfection through 1) differential protein adsorption on nanotopographies compared to micron and unpatterned substrates, 2) modulation of focal adhesion turnover on substrates with different patterns and sizes and 3) different intracellular contractility on different substrates.

Example 5

This example demonstrated the baso-lateral uptake of topographical structures in hMSCs.

Materials and Methods

Fabrication of Collapse Pillar Structures

FIG. 12 illustrates the fabrication of the polystyrene collapse pillar structures using polydimethylsiloxane (PDMS, Dow Corning, Sylgard 184). Upright polystyrene (PS) pillars were first fabricated by nanoimprinting lithography. Polystyrene (PS) (Sigma Aldrich, Mw=45,000 g/mol), and Rhodamine B (Sigma Aldrich, Rhodamine 110 chloride, Mw=366.8 g/mol) were purchased from Sigma Aldrich and used as received. PS films were prepared by spin coating of their solutions (2.5 wt % for PMMA and 23 wt % for PS, in toluene) on silicon substrate at 2000 rpm. Rhodamine B was added as the staining fluorescent dye in PS solutions. The imprinting process of PS was carried out at 180° C. at 60 bars for 10 minutes. To collapse the pillars, a PDMS slab was used. PDMS was mixed at a ratio of 1:10 curing agent to elastomeric base according to the manufacturer's protocol, degassed and cured at 80° C. for 3 hours. The cured PDMS was brought into contact with the top surface of upright PS pillars. A shearing force was then applied parallel to the substrate to overcome the cohesive three between the PS pillars and the imprinted layer. During the process of shearing, collapsed PS pillar will be transferred onto the PDMS, which will be used for the subsequent basal-lateral uptake experiment.

Internalization of Residual Free Pillar and Collapsed Pillar

Human MSCs that were seeded on rhodamine labeled residual free and collapsed pillar structures were stained for F-actin using Oregon Green 488 Phalloidin (Invitrogen Molecular Probe) and counterstained with DAPI. Fluorescently stained hMSCs for F-actin and DAPI were imaged using a laser scanning confocal microscope (Olympus FluoView FV1000). Z-sections of the hMSCs on residual free and collapsed pillar substrates were taken at 0.1 µm and 0.3 µm intervals respectively, for the visualization of collapsed pillars present within hMSCs.

SEM of Cells on Pillars

Samples with hMSCs, COS7 and MCF7 seeded were fixed in 4% PFA, washed in 0.1 M sodium cacodylate, and post-fixed in 2% OsO4 in 0.1 M Na cacodylate, pH 7.2. After post-fixation, the samples were dehydrated in a graded ethanol series. After drying by evaporation of hexamethyldisilazane (HMDS), the samples were sputter-coated with gold and viewed with SEM (SEM, Quanta FEG 200, HV mode) at 10-15 kV.

Results

Figure 7:
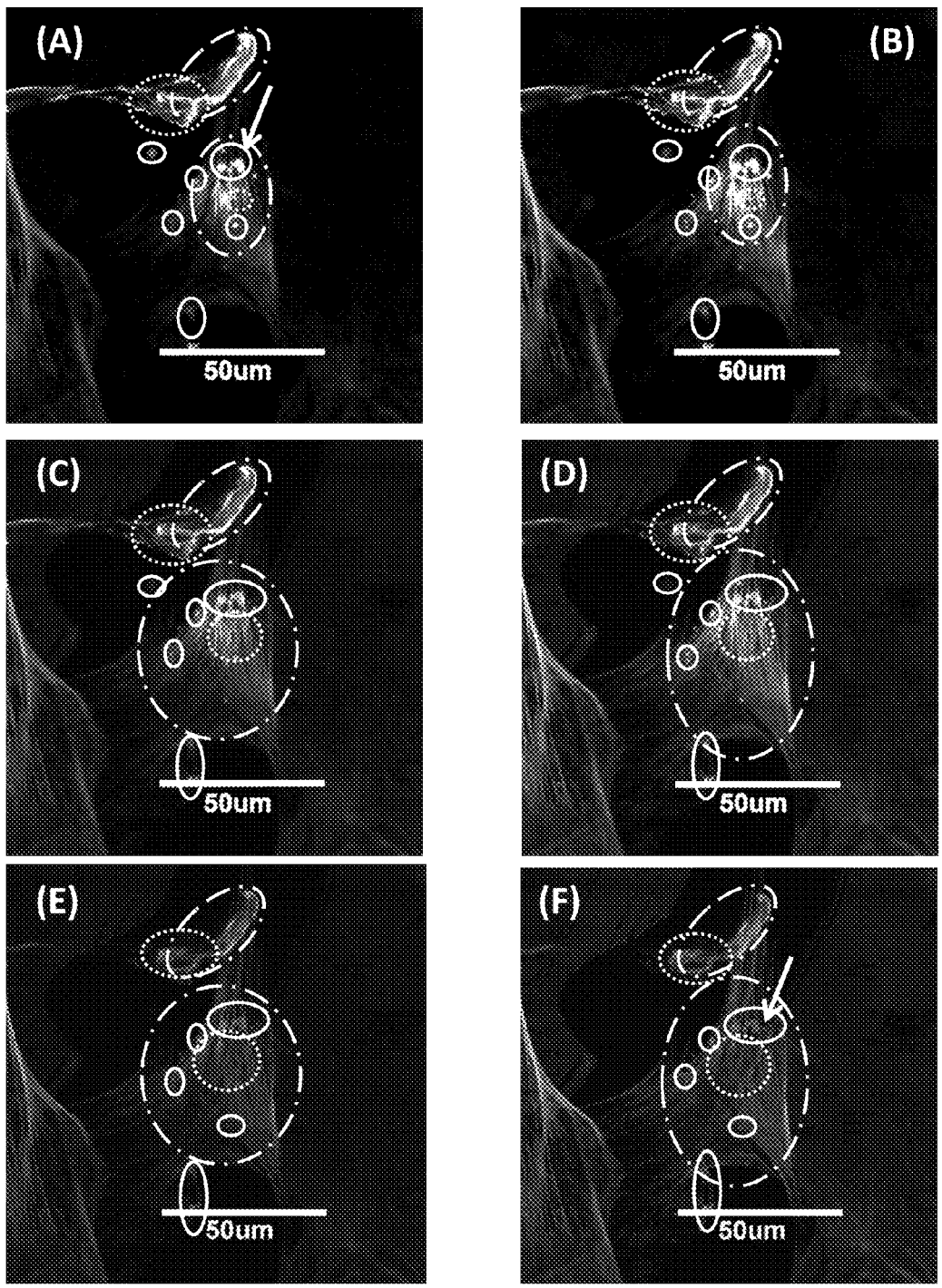
FIG. 7 shows confocal z-stack fluorescent images of hMSCs cultured on 200 nm upright pillars without the residual layer after 24 hours. Each successive image represents a 0.1 µm z-step from the baso-lateral surface to the apical surface of the cell. Cells are stained for actin filaments using Oregon Green 488 Phalloidin (green—circles with interrupted line), DAPI (blue circles with dotted line) and upright 200 nm pillars are rhodamine tagged (red—circles with solid line). Arrows indicate internalized pillars and scale bars represent 50 µm. It can be seen from FIG. 7 that the hMSCs appear to have internalized some of the upright pillars.
Figure 8:
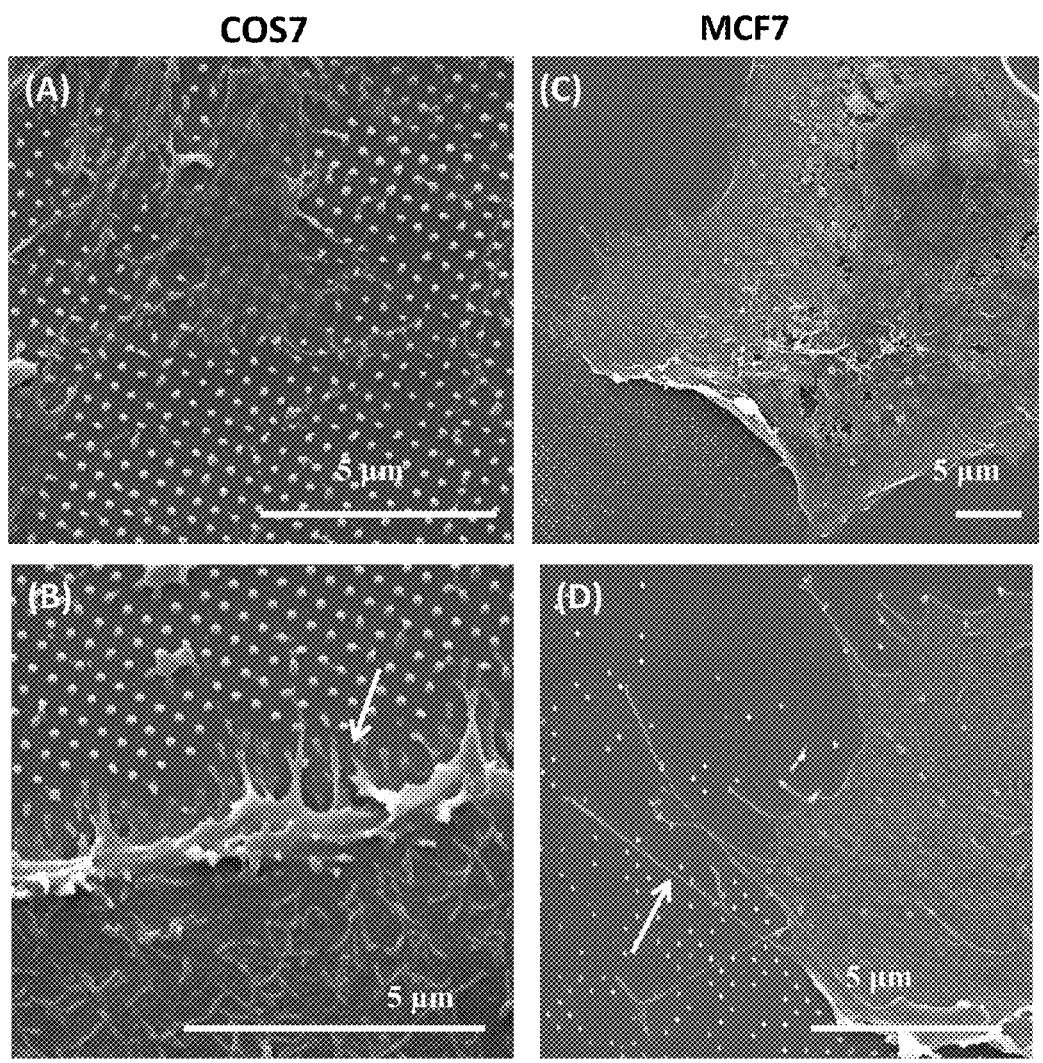
FIG. 8 shows scanning electron microscope images of COS 7 (A-B), MCF7 (C-D) and hMSCs (E-F) cultured on 200 nm upright pillars without the residual layer after 24 hours. It can be seen from FIG. 8 that all cell types show increased filopodia extensions directed towards the nanopillars on these substrates and appear to "grab" the pillars towards themselves, detaching the pillars from the substrate as indicated by arrows seen in E, D and F. It can also be seen that the large numbers of filopodias long extensions were particularly noticeable in hMSCs, (Scale bars=5 µm in each image)
Figure 8:
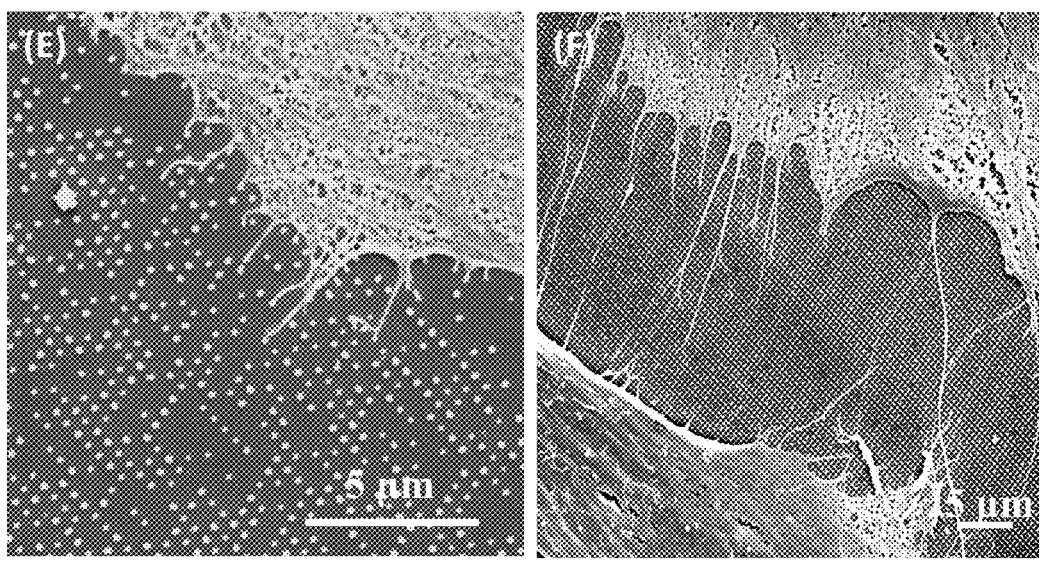
Figure 10:
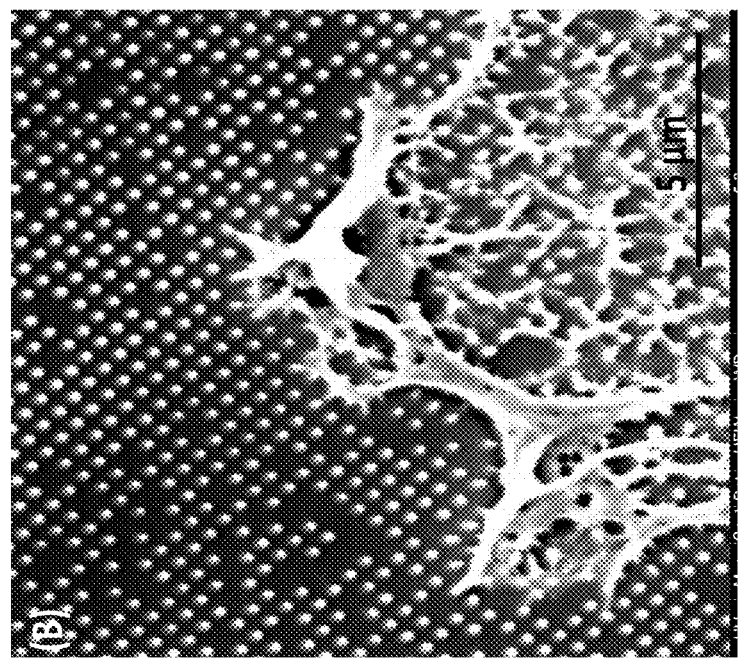
FIG. 10 shows scanning electron microscopy images of hMSCs on 200 nm pillars residual free substrates. It can be seen from A that long filopodia extensions were observed in an attempt by the cells to grab onto these structures while B shows cortical actin was highly expressed in these cells on these substrates.
Figure 10:
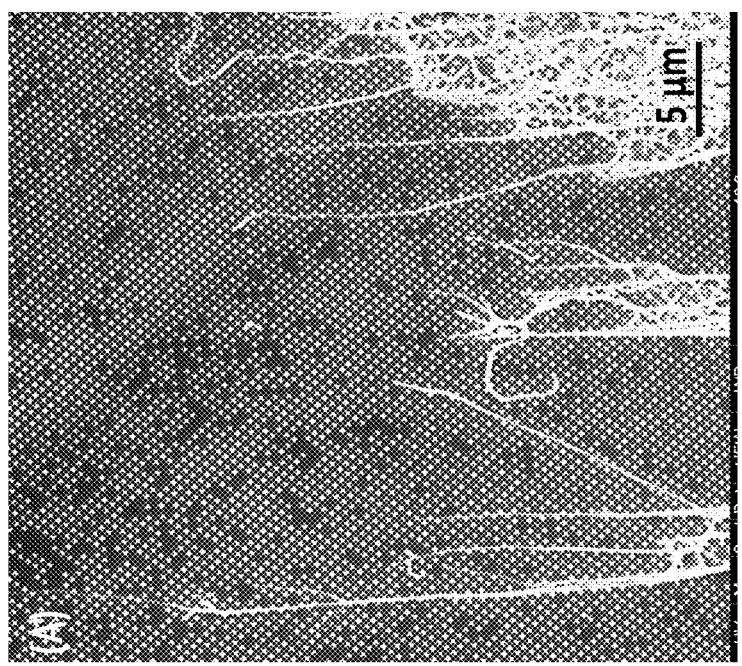
Figure 11:
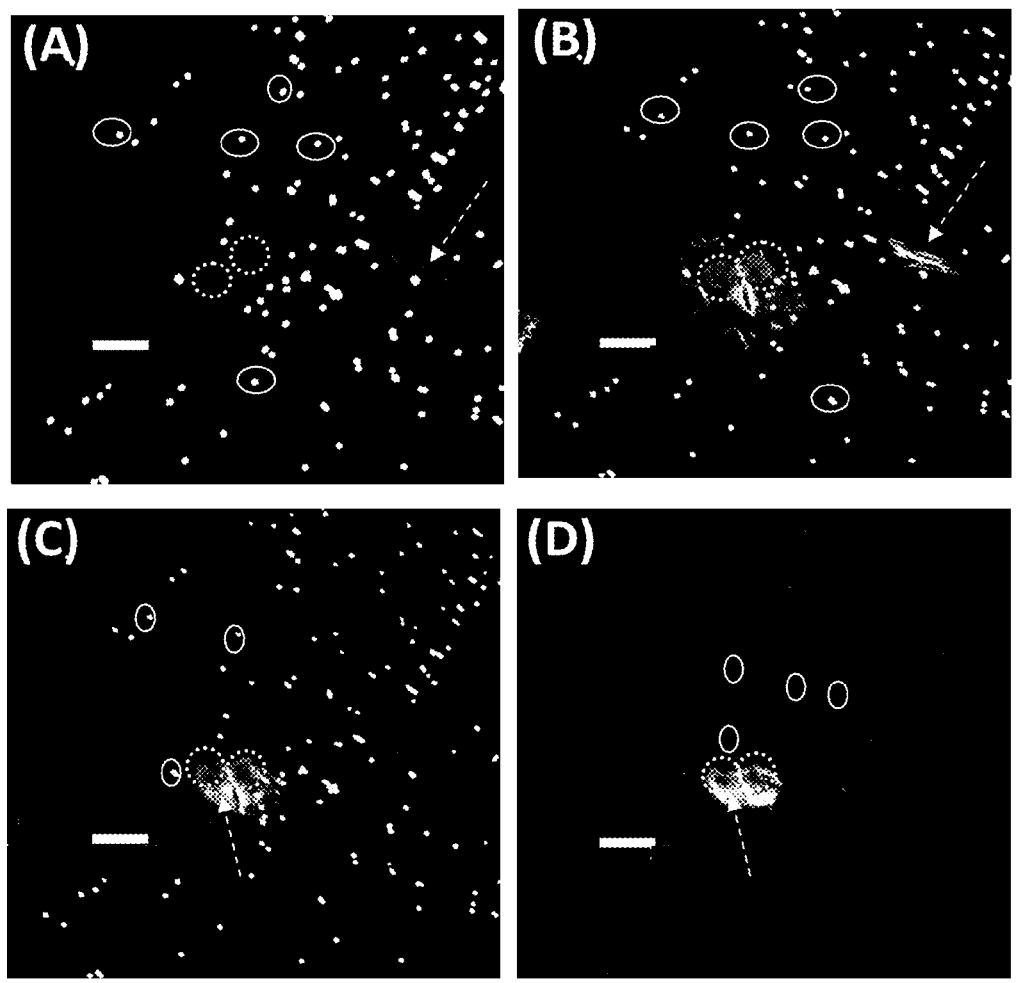
FIG. 11 shows the confocal Z-stack of COS7 (A to D). MCF7 (E to H) and hMSC (I to L) cells cultured on PDMS substrates containing collapsed 2 µm PS pillar structures after 24 hours. Each successive image represents a 0.3 µm z step from the baso-lateral surface to the apical surface of the cell. Cells are stained for actin filaments using Oregon Green 488 Phalloidin (green-dashed arrows), DAPI (blue-circles with dotted lines) and collapsed pillar structures are rhodamine-tagged (red-circles with solid line). Solid arrows indicate pillars that have been internalized and bars represent 20 µm. It can be seen from FIG. 11 that hMSCs appear to have internalized the larger sized 2 µm collapsed pillars.
Figure 11:
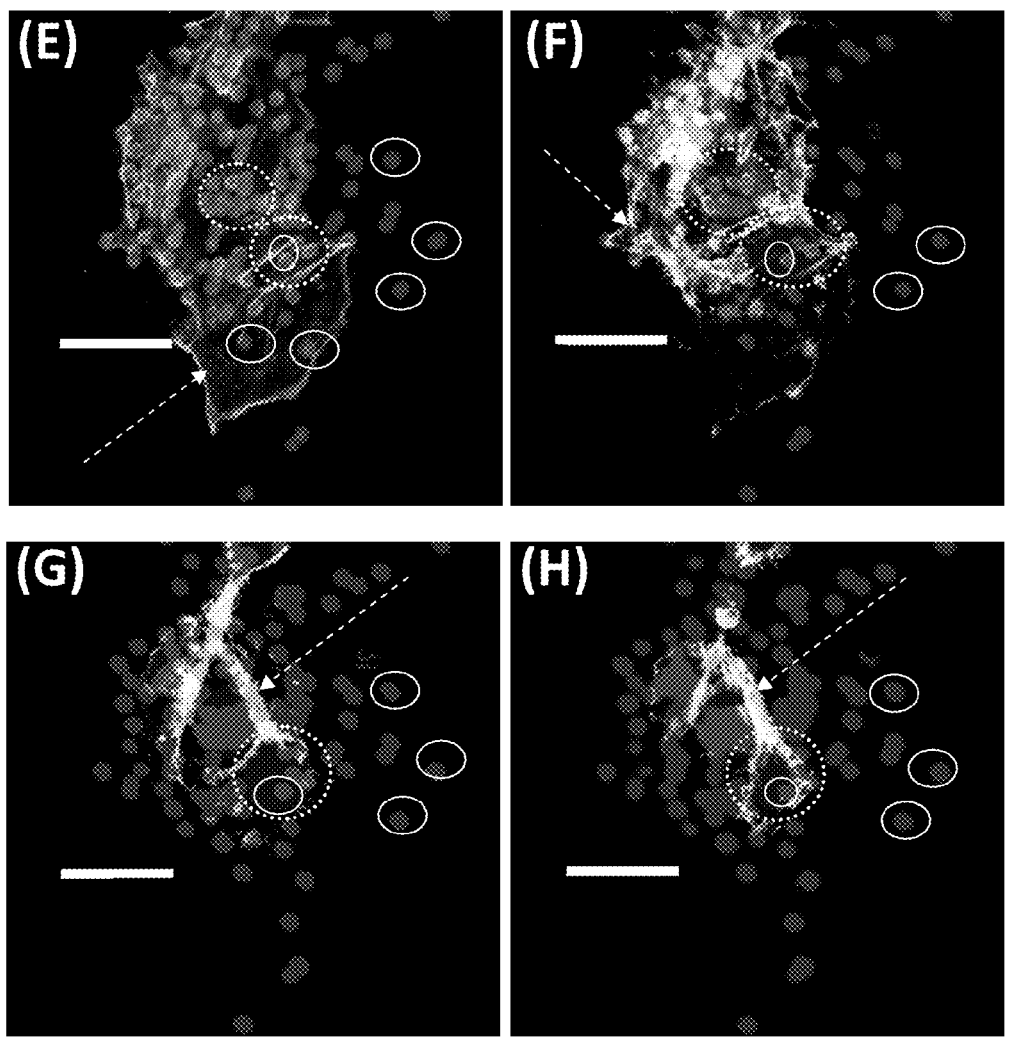
Figure 11:
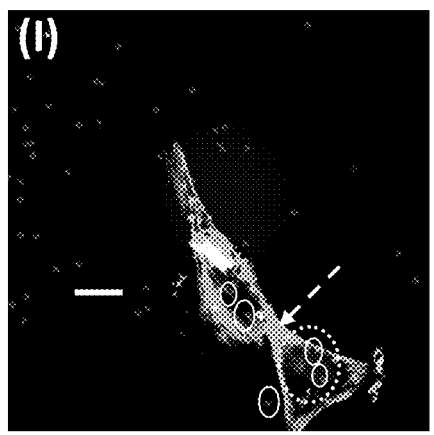
Figure 11:
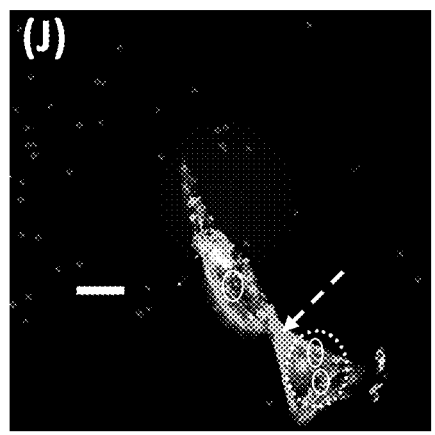
Figure 11:
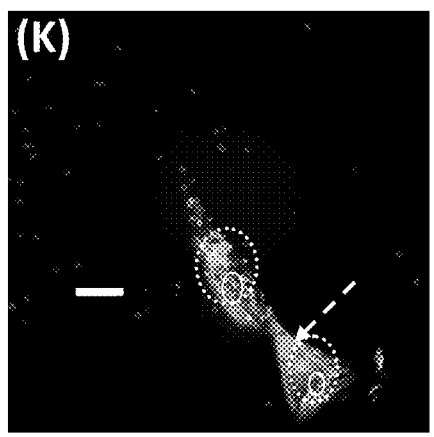
Figure 11:
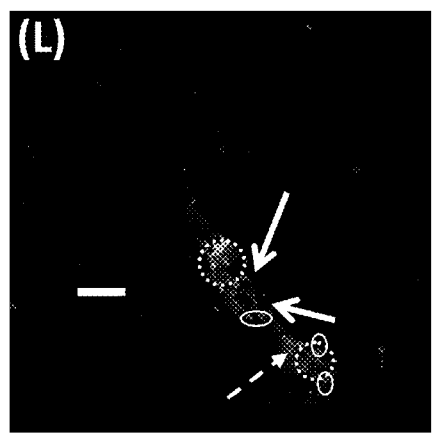

Internalization of 200 nm Residual-Free Upright Pillars hMSCs were cultured onto substrates containing residual-free 200 nm pillars as visualized using confocal microscopy and SEM in FIGS. 7 and 8, respectively. FIG. 7A-F show confocal z-sections in 0.1 µm successive steps of hMSCs fluorescently stained for F-actin and nucleus. A reconstructed 3-D representation of the cell using collected z-stacks showed these structures to be located within the peri-nuclear region of these stem cells (data not shown). Upright pillars without the residual layer were embedded with rhodamine in red to differentiate these structures from cellular organelles and intracellular structures. When the focal planes were moved from the basal surface (maximum pillar signal intensity) to the apical surface (pillars are off focus), intense red fluorescent signals originating from the pillars (denoted by arrows in FIG. 7A-F) appear to remain in focus. The hMSCs appeared to have internalized some of the upright pillars. SEM of the COS7, MCF7 and hMSCs residing on these residual free nano-pillars showed long and extensive filopodia projections (FIG. 8A-F). The close up images of filopodia extensions and cortical actin in hMSCs are shown in FIG. 10. A similar experiment carried out using the collapse pillar structures gave similar results that hMSCs appear to have internalized the larger sized 2 µm collapsed pillars (FIG. 11).

The results from the SEM images (FIG. 8) show that cells extended long filopodia extensions to reach for these nano-sized structures. Filopodia are thin membrane protrusions that act to probe the extracellular environment. Also known as microspikes, these extensions can be found at the migrating front end of cells. The SEM observations indicate that cells were able to specifically target their filopodia onto these nano-sized pillars, affix themselves onto these structures and exert a pulling force onto these structures for cellular locomotion. In the disclosed system of structure internalization, the residual free topographical structures act to provide both topographical cues and a medium of possible drug delivery. The imprinted topographical cues can therefore regulate cellular behaviors including proliferation, spreading and even differentiation in stem cells. Upon exertion of cellular force onto these nanotopographical cues, the imprinted structures can be detached and internalized by the residing cells as a drug delivery system.

These results show an increased cortical actin activity in the cells residing on these particles. Cortical actin plays important roles in clathrin-mediated endocytotic pathways. Earlier studies employing 1 µm cylindrical PRINT particles were shown to be internalizing mainly via clathrin-mediated endocytosis pathways as well as macropinocytosis. However, due to the proximity of the structures to the baso-lateral surface of the residing cells, entry from the apical surface will be little or not significant. Therefore, the internalization of residual free pillars is unlikely to be similar to the previous mentioned study. Nonetheless, the results show that multiple internalized particles were similarly observed. As smaller sized structures were used in this study, it is possible for these particles to gain entry through other pathways.

Internalization of 2 μm Collapsed Pillars.

Adherent cells can undergo endocytosis at both the apical as well as the baso-lateral surface. Accordingly, confocal imaging of fluorescently stained COS7, MCF7 and hMSCs cultured on rhodamine embedded 2 μl pillars after 24 hours incubation was performed (FIG. 11). Each successive image shows 0.3 μm step increase in the z-directions from the maximal red intensity indicating the focal plane of the collapsed pillars to the apical surface of the cells. F-actin was stained using Oregon Green 488 Phalloidin while the nuclei were counterstained with DAN.

Confocal imaging of COS7 and MCF7 cells (FIG. 11E-H) on these collapsed structures did not show any form of cellular internalization although a large number of pillars appear to reside in the baso-lateral surface of the MCF7 cells, as indicated by the red fluorescence intensity. This suggests the attempted endocytosis of these structures may be hindered due to the size.

On the other hand, the hMSCs cultured on these collapsed structures appeared to internalize some of these collapsed structures. It can also be observed that most of the internalized particles reside within the peri-nuclear region of these stem cells as indicated by the white arrows in FIG. 11L. Pillars indicated by red intensity appeared to remain in focus when the focal plane was adjusted towards the apical surface of the cells where surrounding pillars that were not internalized became out of focus (FIG. 11I-K).

This study employing 2 μm collapsed structures allows cells to undergo particle internalization by exerting less pulling force to "self-detach" the collapsed topographical structures. The results indicate that cells were able to internalize larger sized collapsed structures compared to residual free nanostructures as the adhesion forces between the structures and the underlying substrates were much reduced. The preferential internalization by hMSCs might also be due to the larger intracellular contractility present in hMSCs. The careful design of these substrates can thus be used for specific trafficking in a target population within a mixed population.

The invention claimed is:

1. A construct for promoting absorption of molecules by a cell located at the surface of the construct; wherein the construct comprises:
a plurality of protrusions located at the surface of the construct;
wherein the protrusions are in the form of pillars having a diameter of between about 200 nm to about 2 μm;
wherein the pitch between the protrusion from edge to edge is between 150 to 300 nm such that the pitch between the protrusions is less than the size of the cells to be located at the surface of the construct;
wherein the protrusions have a size and are spaced apart from each other at a distance that promotes absorption of molecules by said cell and wherein the absorption of molecules is facilitated by endocytosis, or receptor mediated endocytosis, or pinocytosis, or phagocytosis;
wherein the pillars are collapsed pillars lying at the surface of the construct; and
wherein the collapsed pillars have a length of between about 50 nm to about 5 μm.

2. The construct of claim 1, wherein the protrusions are arranged in an isotropic pattern.

3. The construct of claim 1, wherein the protrusions are arranged in an anisotropic pattern.

4. The construct of claim 1, wherein the protrusions are located at the surface of the construct in a detachable form.

5. The construct of claim 1, wherein the protrusions are located at the surface of the construct in a non-detachable form.

6. The construct of claim 1, wherein the protrusions are round.

7. The construct of claim 1, wherein the protrusions are polygonal.

8. The construct of claim 1, wherein the pillars are extend about 50 nm to 4 μm, or about 100 nm to about 2 μm above the surface of the construct.

9. The construct of claim 1, wherein the pitch between the pillars from edge to edge is between 200 nm to 250 nm.

10. The construct of claim 1, wherein a residual layer is arranged between the pillars and the surface of the construct.

11. The construct of claim 1, wherein the construct is obtained via nano-imprinting lithography.

12. The construct of claim 11, wherein the nano-imprinting lithography is thermal nano-imprinting lithography or UV nano-imprinting lithography.

13. The construct of claim 11, wherein the construct and/or the protrusions are made of a polymer.

14. The construct of claim 13, wherein the polymer is a synthetic polymer, or a rigid synthetic polymer, or a bioresorbable polymer, or a biodegradable polymer.

15. The construct of claim 14, wherein the synthetic polymer is selected from the group consisting of poly (methyl methacrylate) (PMMA), polydimethylsiloxane (PDMS), polystyrene (PS) and mixtures thereof.

16. The construct of claim 15, wherein the polystyrene is tissue-culture grade polystyrene (TCPS).

17. The construct of claim 14, wherein the biodegradable polymer is selected from the group consisting of chitosan, poly(ε-caprolactone), polyglycolic acid, poly(lactic acid), polyphosphoester (PPE) and mixtures thereof.

18. The construct of claim 14, wherein the rigid synthetic polymer is polystyrene.

19. The construct of claim 13, wherein during manufacture the polymer is mixed with molecules which are to be absorbed by the cell to be located on the construct.

20. The construct of claim 13, wherein the molecules are attached to the surface of the protrusions.

* * * * *